(12) United States Patent  
Buchbinder et al.

(10) Patent No.: US 10,814,317 B2  
(45) Date of Patent: Oct. 27, 2020

(54) HYDROCARBON PROCESSES USING HALOMETALLATE IONIC LIQUID MICRO-EMULSIONS

(71) Applicant: UOP LLC, Des Plaines, IL (US)

(72) Inventors: Avram M. Buchbinder, Skokie, IL (US); Hayim Abrevaya, Kenilworth, IL (US); Gavin P. Towler, Inverness, IL (US)

(73) Assignee: UOP LLC, Des Plaines, IL (US)

( * ) Notice: Subject to any disclaimer, the term of this patent is extended or adjusted under 35 U.S.C. 154(b) by 141 days.

(21) Appl. No.: 16/128,151

(22) Filed: Sep. 11, 2018

(65) Prior Publication Data

US 2019/0001314 A1    Jan. 3, 2019

Related U.S. Application Data

(60) Division of application No. 15/713,017, filed on Sep. 22, 2017, now Pat. No. 10,596,561, which is a (Continued)

(51) Int. Cl.  
*C07C 2/54* (2006.01)  
*B01J 31/02* (2006.01)  
(Continued)

(52) U.S. Cl.  
CPC ....... *B01J 31/0288* (2013.01); *B01J 31/0281* (2013.01); *B01J 31/0284* (2013.01); (Continued)

(58) Field of Classification Search  
None  
See application file for complete search history.

(56) References Cited

U.S. PATENT DOCUMENTS 7,553,406 B2    6/2009  Wasserscheid et al.  
8,163,856 B2    4/2012  Bergman et al.  
(Continued)

FOREIGN PATENT DOCUMENTS

CN    101274249 B    3/2011  
CN    101244972 B    5/2012  
(Continued)

OTHER PUBLICATIONS

Blahusiak, "Physical properties of phosponium ionic liquid and its mixtures with dodecane and water", J. Chem. Thermodynamics 72 (2014) 54-64.

(Continued)

*Primary Examiner* — Philip Y Louie

(57) ABSTRACT

A process utilizing a micro-emulsion is described. The micro-emulsion formed by contacting an ionic liquid, a co-solvent, a hydrocarbon, an optional surfactant, and an optional catalyst promoter to form the micro-emulsion. The micro-emulsion comprises a hydrocarbon component comprising the hydrocarbon and an ionic liquid component comprising the ionic liquid. The ionic liquid comprises a halometallate anion and a cation. The co-solvent has a polarity greater than a polarity of the hydrocarbon. The ionic liquid is present in an amount of 0.05 wt % to 40 wt % of the micro-emulsion. A product mixture comprising a product is produced in a process zone containing the micro-emulsion.

20 Claims, 4 Drawing Sheets

Related U.S. Application Data continuation of application No. PCT/US2016/025415, filed on Mar. 31, 2016.

(60) Provisional application No. 62/141,087, filed on Mar. 31, 2015.

(51) Int. Cl.
  *B01J 35/00* (2006.01)
  *C07C 2/00* (2006.01)

(52) U.S. Cl.
  CPC ....... *B01J 31/0289* (2013.01); *B01J 35/0013* (2013.01); *C07C 2/00* (2013.01); *B01J 31/0277* (2013.01)

(56) References Cited

U.S. PATENT DOCUMENTS

| | | |
|---|---|---|
| 8,198,499 B2 | 6/2012 | Luo et al. |
| 8,535,650 B2 | 9/2013 | Constantinides et al. |
| 2005/0119423 A1 | 6/2005 | Bergman et al. |
| 2006/0120213 A1 | 6/2006 | Tonkovich et al. |
| 2007/0142213 A1 | 6/2007 | Harris et al. |
| 2008/0024104 A1 | 1/2008 | Yamada |
| 2010/0197483 A1 | 8/2010 | Elomari et al. |
| 2011/0217553 A1 | 9/2011 | Warner et al. |
| 2012/0121485 A1 | 5/2012 | Rogers et al. |
| 2013/0066130 A1 | 3/2013 | Luo et al. |

FOREIGN PATENT DOCUMENTS

| | | |
|---|---|---|
| EP | 1920824 A1 | 5/2008 |
| RU | 46542 U1 | 7/2005 |
| WO | 9521872 A1 | 8/1995 |
| WO | 2003089390 A3 | 10/2003 |
| WO | 2006111712 A3 | 10/2006 |
| WO | 2006131699 A1 | 12/2006 |
| WO | 2010135064 A2 | 11/2010 |
| WO | 2012009031 A2 | 1/2012 |
| WO | 2013183137 A1 | 12/2013 |
| WO | 2016161197 A1 | 10/2016 |
| WO | 2016161199 A1 | 10/2016 |
| WO | 2016161200 A1 | 10/2016 |
| WO | 2016161202 A1 | 10/2016 |
| WO | 2016161203 A1 | 10/2016 |
| WO | 2016161204 A1 | 10/2016 |
| WO | 2016161206 A1 | 10/2016 |
| WO | 2016161208 A1 | 10/2016 |

OTHER PUBLICATIONS

Chandran, "Self-Assembled Inverted Micelles Stabilize Ionic Liquid Domains in Supercritical CO2", J. Am. Chem. Soc. 2010, 132, 12511-12516.

Cheng, "Self-Assembly of Imidazolium-Based Rodlike Ionic Liquid Crystals: Transition from Lamellar to Micellar Organization", Chem. Eur. J. 2010, 16, 4588-4601.

Chen, "Solubility measurements of isobutane/alkenes in sulfuric acid: applications to alkylation", Applied Catalysis A: General 255 (2003) 231-237.

Cong, "Isobutane/2-Butene Alkylation Catalyzed by Strong Acids in the Presence of Ionic Liquid Additives", Petroleum Science and Technology, 32:1981-1987, 2014.

Correa, "Nonaqueous Polar Solvents in Reverse Micelle Systems", Chem. Rev. 2012, 112, 4569-4602.

Eggers, "Enzymatic production of L-tryptophan in a reverse micelle reactor", Bioprocessing Engineering 3 (1988)83-91.

Gayet, "Surfactant Aggregates in Ionic Liquids and Reactivity in Media", International Journal of Chemical Reactor Engineering (2010), vol. 8, 17 pages.

Huang, "Improved catalytic lifetime of H2SO4 for isobutane alkylation with trace amount of ionic liquids buffer", Industrial & Engineering Chemistry Research (2015), Web publication, 1-27.

Rai, "Ethanol-Assisted, Few Nanometer, Water-In-Ionic-Liquid Reverse Micelle Formation by a Zwitterionic Surfactant", Chem. Eur. J. 2012, 18, 12213-12217.

Rojas, "Nonaqueous Microemulsions Based on N,N'-Alkylimidazolium Alkylsulfate Ionic Liquids", Langmuir 2013, 29, 6833-6839.

Uskokovic, "Reverse micelles: Inert nano-reactors or physico-chemically active guides of the capped reactions", Advances in Colloid and Interface Science 133 (2007) 23-34.

Xue, "Choline acetate enhanced the catalytic performance of Candida rogusa lipase in AOT reverse micelles", Colloids and Surfaces B: Biointerfaces 105 (2013) 81-86.

Yang, "Study on Enzymatic Activity and Stability in Different Reaction Media", from Henan Huagong (2008), 25(9), 1-5. | Language: Chinese, Database: CAPLUS.

Zhao, "Liquid Crystalline Phases Self-Organized from a Surfactant-like Ionic Liquid C16mimCl in Ethylammonium Nitrate", J. Phys. Chem. B 2009, 113, 2024-2030.

Search Report dated Jun. 30, 2016 for corresponding PCT Appl. No. PCT/US2016/025415.

U.S. Appl. No. 62/141,056, filed Mar. 31, 2015.
U.S. Appl. No. 62/141,070, filed Mar. 31, 2015.
U.S. Appl. No. 62/141,076, filed Mar. 31, 2015.
U.S. Appl. No. 62/141,087, filed Mar. 31, 2015.

Li, "Compressed CO2-enhanced solubilization of 1-butyl-3-methylimidazolium tetrafluoroborate . . . " Journal of Chemical Physics (2004), 121(15), 7408-7412.

Li, "Nonaqueous microemulsion-containing ionic liquid [bmim][PF6] as polar microenvironment", Colloid and Polymer Science (2005), 283(12), 1371-1375.

Falcone, "On the formation of new reverse micelles: A comparative study of benzene/surfactants/ionic liquids . . . ", Langmuir (2009), 25(18), 10426-10429.

Moniruzzaman, "Formation of reverse micelles in a room-temperature ionic liquid", ChemPhysChem (2008), 9(5), 689-692.

International Search report for international application No. PCT/US2016/025411, dated Jul. 14, 2016.
International Search report for international application No. PCT/US2016/025414, dated Jul. 14, 2016.
International Search report for international application No. PCT/US2016/025421, dated Jun. 23, 2016.
International Search report for international application No. PCT/US2016/025419, dated Jun. 30, 2016.
International Search report for international application No. PCT/US2016/025425, dated Jul. 14, 2016.
International Search report for international application No. PCT/US2016/025429, dated Aug. 18, 2016.
International Search report for international application No. PCT/US2016/025422, dated Jun. 30, 2016.
International Search report for international application No. PCT/US2016/025415, dated Jun. 30, 2016.

HYDROCARBON PROCESSES USING HALOMETALLATE IONIC LIQUID MICRO-EMULSIONS

CROSS-REFERENCE TO RELATED APPLICATIONS

This application is a Divisional of copending U.S. application Ser. No. 15/713,017, filed Sep. 22, 2017, which is a Continuation of International Application No. PCT/US2016/025415 filed Mar. 31, 2016, which application claims priority from U.S. Provisional Application No. 62/141,087 filed Mar. 31, 2015, now expired, the contents of which cited applications are hereby incorporated by reference in their entirety.

BACKGROUND OF THE INVENTION

In liquid-liquid reactions, an intrinsic tradeoff exists between reactivity and post-reaction separation. High interfacial surface area between two liquid phases is needed to achieve high activity. As an example, for motor fuel alkylation using ionic liquid catalysts, large ionic liquid droplets implies low surface area, which leads to slow mass transfer of olefin and isobutane from the bulk hydrocarbon phase to the ionic liquid droplets, and a mass transfer-limited reaction of olefin inside the ionic liquid droplets. Mass transfer limitations also lead to slow product mass transfer out of the ionic liquid droplets back to the hydrocarbon phase and to product degradation, hence to low $C_8$ alkylate selectivities.

High ionic liquid inventory and/or smaller ionic liquid droplets are used to counter the mass transfer limitations of the alkylation kinetics. However, smaller droplets which are typically generated by shear force, are also more difficult to separate than larger droplets once the reaction is complete. Small ionic liquid droplets require very long or even infinite settling times for complete separation by gravity. Often, specialized equipment such as coalescers or centrifugal separation may be employed. However, coalescers are subject to fouling by pinning of ionic liquid droplets on coalescing elements and separation by centrifugal force requires a large amount of power.

The high activity of ionic liquids used for motor fuel alkylation and related processes allows for the use of relatively low ionic liquid volume fractions compared to the high acid volume fractions used in HF or $H_2SO_4$ processes. However, even at low ratios of ionic liquid catalyst to hydrocarbon, the loss rates of ionic liquid due to inefficient separation and deactivation may introduce a significant cost in ionic liquid catalyst make-up.

Alternative methods for generating liquid-liquid mixtures which allow both efficient reaction and easy separation after the reaction is over are needed for alkylation and for other liquid-liquid reactions.

SUMMARY OF THE INVENTION

One aspect of the invention is a micro-emulsion. In one embodiment, the micro-emulsion comprises a hydrocarbon component comprising a hydrocarbon and an ionic liquid component comprising an ionic liquid. The micro-emulsion can include an optional surfactant, and an optional catalyst promoter. The co-solvent has a polarity greater than the polarity of the hydrocarbon. The ionic liquid comprises a halometallate anion and a cation, and the ionic liquid is present in an amount of about 0.05 wt % to about 40 wt % of the micro-emulsion.

Another aspect of the invention is a method of forming a micro-emulsion. In one embodiment, the method involves contacting the hydrocarbon, the co-solvent, the ionic liquid, the optional surfactant, and the optional catalyst promoter to form the micro-emulsion. The micro-emulsion comprises a hydrocarbon component comprising the hydrocarbon and an ionic liquid component comprising the ionic liquid. The co-solvent has a polarity greater than the polarity of the hydrocarbon. The ionic liquid comprises a halometallate anion and a cation. The ionic liquid is present in an amount of about 0.05 wt % to about 40 wt % of the micro-emulsion.

Another aspect of the invention is a process utilizing a micro-emulsion. In one embodiment, the process includes forming a micro-emulsion by contacting an ionic liquid, a co-solvent, a hydrocarbon, an optional surfactant, and an optional catalyst promoter. The micro-emulsion comprises a hydrocarbon component comprising the hydrocarbon and an ionic liquid component comprising the ionic liquid. The ionic liquid comprises a halometallate anion and a cation. The co-solvent has a polarity greater than a polarity of the hydrocarbon. The ionic liquid is present in an amount of 0.05 wt % to 40 wt % of the micro-emulsion. In some embodiments the polar structures comprise reverse micelles. Other features include the ionic liquid being at least slightly soluble in the oil phase, the hydrocarbon having a polarity lower than a polarity of the co-solvent, the co-solvent being miscible in the oil phase, and the oil phase comprising at least about 50 vol % of the micro-emulsion. A product mixture comprising a product is produced in a process zone containing the micro-emulsion. For example, the process can be a hydrocarbon conversion process in which the ionic liquid in the micro-emulsion catalyzes a reaction, or a separation process.

Another aspect of the invention is an alkylation process. In one embodiment, the alkylation process comprises: passing a micro-emulsion to an alkylation reactor, the micro-emulsion formed by: contacting an ionic liquid, a co-solvent, an isoparaffin, an optional surfactant, and an optional catalyst promoter to form the micro-emulsion, the micro-emulsion comprising: a hydrocarbon component comprising the isoparaffin, the isoparaffin having from 4 to 10 carbon atoms; an ionic liquid component comprising the ionic liquid, the ionic liquid comprising a halometallate anion and a cation; a co-solvent having a polarity greater than a polarity of the isoparaffin, the ionic liquid being present in an amount of about 0.05 wt % to about 40 wt % of the micro-emulsion; and passing an olefin having from 2 to 8 carbon atoms to the alkylation reactor containing the micro-emulsion, wherein the alkylation reactor is operated at alkylation reaction conditions to react the olefin and the isoparaffin to generate a reaction mixture comprising an alkylate.

DETAILED DESCRIPTION OF THE INVENTION

Figure 1:
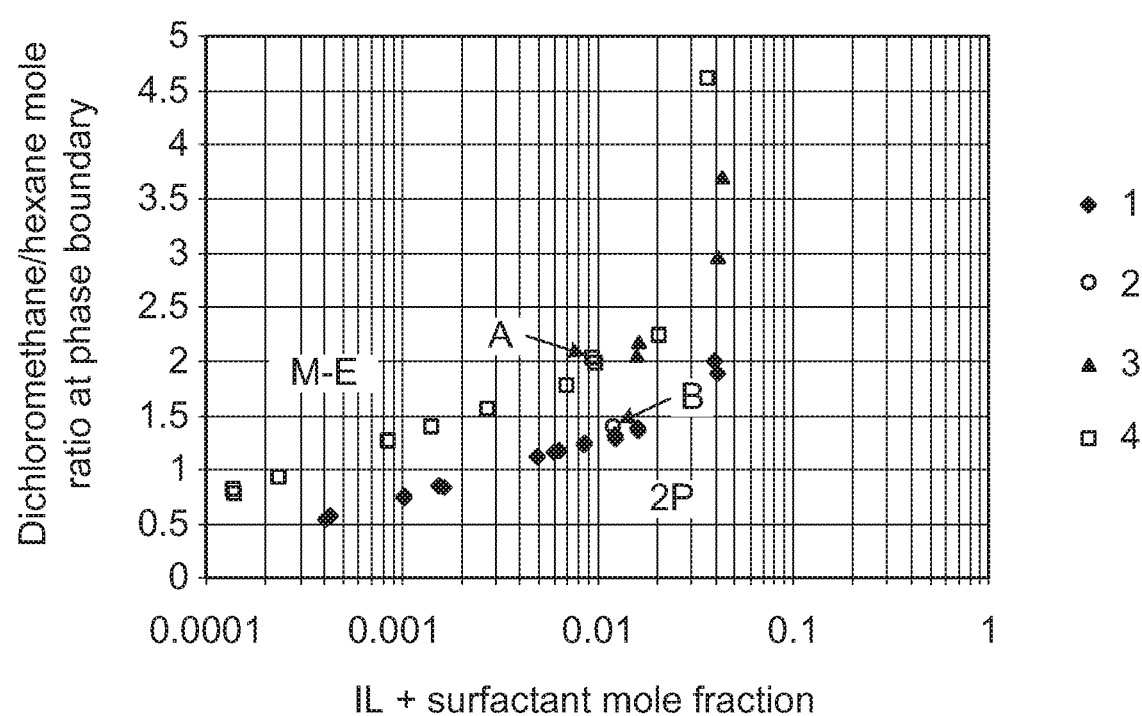
FIG. 1 is a phase diagram showing the dichloromethane/hexane mole ratio as a function of total ionic liquid plus surfactant mole fraction.

One aspect of the invention is a micro-emulsion composition composed at least partially of an ionic liquid in a mixture that contains a hydrocarbon. Rather than relying on the continuous input of force to shear the ionic liquid and create droplets, the micro-emulsion comprises thermodynamically stable structures in a less-polar medium. Although not wishing to be bound by theory, it is believed that the structures are stabilized by an amphiphilic surfactant or the ionic liquid itself.

The micro-emulsion contains a hydrocarbon component comprising a hydrocarbon having a polarity, an ionic liquid component comprising an ionic liquid, the ionic liquid comprising a halometallate anion and a cation, and a co-solvent having a polarity greater than the polarity of the hydrocarbon. The micro-emulsion can be reverse micelles, micelles, or a bi-continuous micro-emulsion. The ionic liquid component typically contains a higher content of co-solvent than the hydrocarbon component.

Reverse micelles are small structures containing an amphiphile, which allows for dispersion of a polar substance in a less-polar liquid. Such micro-emulsions are well known. Commonly, a micro-emulsion containing reverse micelles contains small structures on the order of one to tens of nanometers which consist of a water core surrounded by a surfactant in an organic solvent. Mixtures containing ionic liquid reverse micelles have been made. See, for example, Table 5 of Correa et al., Nonaqueous Polar Solvents in Reverse Micelle Systems, CHEM. REV. 2012, vol. 112, p. 4569-4602, which summarizes this work. Previous examples of ionic liquid reverse micelles generally contain a surfactant in addition to the ionic liquid. Furthermore, the prior art does not address the use of halometallate ionic liquids, which are often used in their Lewis acidic form. Such ionic liquids are very useful for catalytic applications including motor fuel alkylation, but they are also highly reactive and are not compatible with most protic or oxygenated solvents or surfactants.

In some embodiments of this invention, the micro-emulsion comprises reverse micelles. In these embodiments, the co-solvent is miscible in the hydrocarbon and at least a portion of the co-solvent is contained in the hydrocarbon component. The ionic liquid component is dispersed in the hydrocarbon component. The ionic liquid component is more polar than the hydrocarbon component.

In some embodiments, the micro-emulsion comprises micelles. With micelles, there is a core of the hydrocarbon component surrounded by the ionic liquid component and an optional surfactant. The hydrocarbon component core surrounded by the ionic liquid component and the optional surfactant is dispersed in a polar continuous medium which comprises the co-solvent. The co-solvent is more polar than the hydrocarbon component.

In some embodiments, the micro-emulsion comprises a bi-continuous micro-emulsion comprising the hydrocarbon component and the ionic liquid component. The ionic liquid component contains at least a portion of the co-solvent, and it is more polar than the hydrocarbon component.

In conventional liquid-liquid mixtures containing ionic liquids and hydrocarbons, where shear force is used to generate droplets in a two-phase mixture, ionic liquid solubility in the non-ionic liquid phase is typically very low. This can be characterized by the solubility of the ionic liquid in a typical non-polar hydrocarbon such as n-hexane. The ionic liquid has a solubility in n-hexane of less than about 5 wt %, or less than about 3 wt %, or less than about 1 wt %, or less than about 0.5 wt %, or less than about 0.1 wt %, or less than about 0.01 wt %. As an example, ionic liquids with halometallate anions have very low solubility in hydrocarbons such as n-hexane and are often characterized as immiscible with hexane, such as in Zhao, D; Wu, M; Kou, Y; Min, E, Catalysis Today, 2002, 74, 157-189 Table 2. As such, these ionic liquids do not form solutions or micro-emulsions when combined with non-polar hydrocarbons, but instead form two-phase systems, with the non-polar hydrocarbon phase being substantially free of ionic liquid. By substantially free we mean that the non-polar hydrocarbon phase contains less than about 5 wt %, or less than about 3 wt %, or less than about 1 wt %, or less than about 0.5 wt %, or less than about 0.1 wt %, or less than about 0.01 wt %. Therefore, in order to form a micro-emulsion, an additional component such as a surfactant and/or a co-solvent must be added. In the present invention, micro-emulsions can be made using an ionic liquid, a hydrocarbon, and a co-solvent. The micro-emulsion may optionally contain an additional surfactant and/or a catalyst promoter.

The hydrocarbon and co-solvent each have a polarity. The polarity of the co-solvent is greater than the polarity of the hydrocarbon. Many hydrocarbons, including those in some embodiments of this invention, have polarity close to zero. Many polarity scales are known. Here polarity is defined by the polarity index P', which is a measure of interactions of a solute relative to other solvents based on solubility constants. This polarity scale is commonly used to distinguish solvents by polarity for predicting solubility. Some hydrocarbons on this scale have P' less than zero. Hydrocarbons with P less than zero are considered to have polarity less than the polarity of the co-solvent if the co-solvent has P' greater than P' of the hydrocarbon. A detailed description of polarity index is found in Snyder, L. R; Journal of Chromatography, 1974, vol 92, pp. 223-230 and tabulation of polarity index for many liquids is found in table I of that reference, which is incorporated herein by reference. For example, polarity index of n-hexane is 0.0, n-decane is −0.3, toluene is 2.3, benzene is 3.0, and methylene chloride (dichloromethane) is 3.4. In the absence of an available polarity index measurement, relative polarity of two liquids is determined from the magnitude of the liquids' dielectric constants. For instance, isobutane has dielectric constant of 1.8 at 300 K (Hayn, W. M, J. Chem. Eng. Data, 1983, vol 28, pp. 367-369), while the dielectric constant of dichloromethane at 298 K is 9.14 (Dean, J. A; Lange's Handbook of Chemistry and Physics, $14^{th}$ ed, p. 5.101, McGraw-Hill, 1992, New York).

In some embodiments, the micro-emulsion can be made utilizing a surfactant that is compatible with the ionic liquid, while in others, no additional surfactant is used. In the latter case, although not wishing to be bound by theory, it is believed that the ionic liquid itself acts as the amphiphile to stabilize the micro-emulsions. To generate a micro-emulsion using a hydrocarbon as a major component of the mixture, a polar aprotic co-solvent such as dichloromethane is used. The micro-emulsions are useful as high surface-area catalysts for alkylation and other hydrocarbon conversion processes, as well as separation processes.

Figure 2:
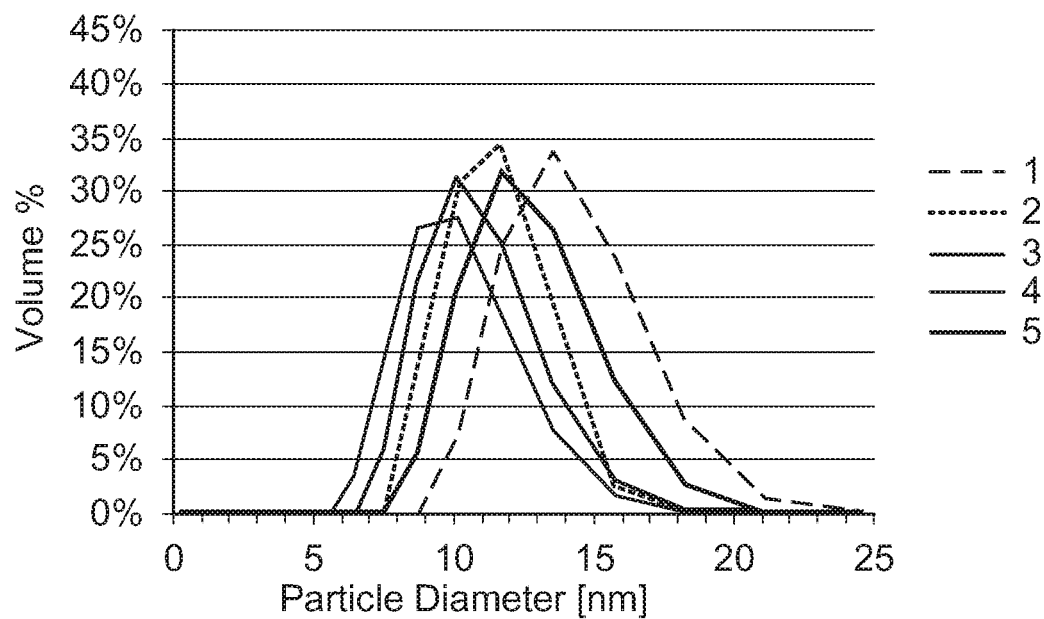
FIG. 2 is a graph showing the volume normalized particle size distribution of a composition containing reverse micelles made using an added surfactant.
Figure 3:
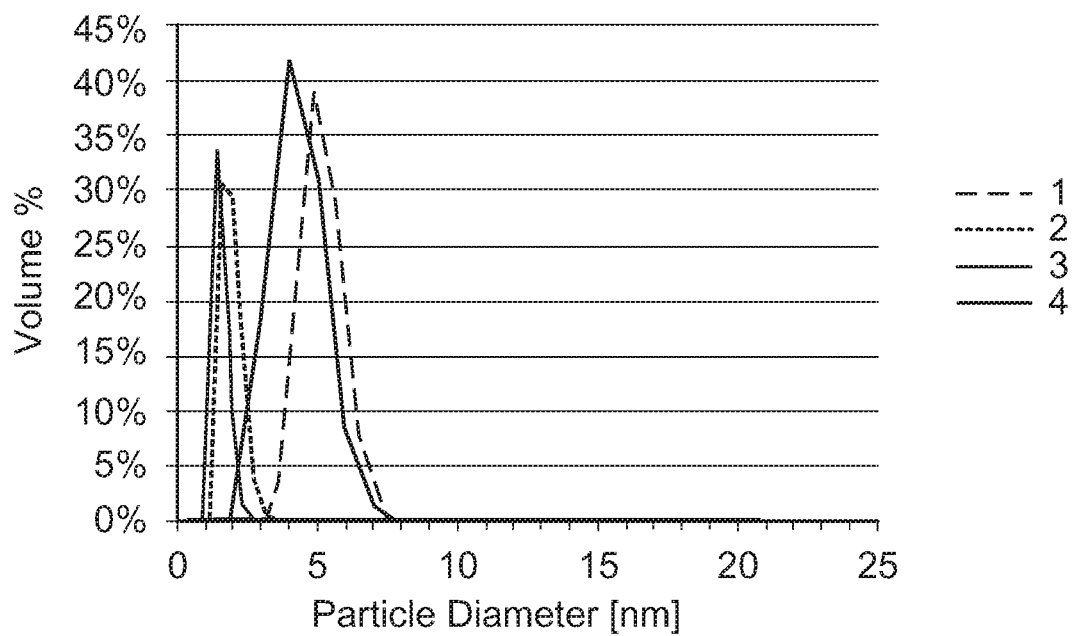
FIG. 3 is a graph showing the volume normalized particle size distribution of a composition containing reverse micelles made without an added surfactant.

In some embodiments, more than about 90% of the reverse micelles or micelles have a diameter less than about 100 nanometers, or less than about 90 nanometers, or less than about 80 nanometers, or less than about 70 nanometers, or less than about 60 nanometers, or less than about 50 nanometers, or less than about 40 nanometers, or less than about 30 nanometers, or less than about 20 nanometers, or about 1 nanometer to about 100 nanometers or about 1 nanometer to about 80 nanometers or about 1 nanometer to about 60 nanometers or about 1 nanometer to about 40 nanometers or about 1 nanometer to about 20 nanometers or about 1 nanometer to about 10 nanometers or about 1 nanometer to about 4 nanometers. The reverse micelles or micelles are typically at least about 1 nanometer in diameter. The presence of added surfactant can be used to help control the size of the reverse micelles or micelles, as shown in FIGS. 2-3. When an added surfactant is present, the reverse micelles or micelles may be larger. In some embodiments, reverse micelles or micelles with added surfactant have diameters about 2 to about 7 times larger than similar compositions without added surfactant. Not wishing to be bound by theory, the presence of an added surfactant may increase the surface tension of the reverse micelles or micelles and allow larger reverse micelles or micelles to be thermodynamically stable. In some embodiments, when an additional surfactant is present, more than about 90% of the reverse micelles or micelles have a diameter in the range of about 3 nanometers to about 100 nanometers, or about 3 nanometers to about 90 nanometers, or about 3 nanometers to about 80 nanometers, or about 3 nanometers to about 70 nanometers, or about 3 nanometers to about 60 nanometers, or about 3 nanometers to about 50 nanometers, or about 3 nanometers to about 40 nanometers, or about 3 nanometers to about 30 nanometers, or about 3 nanometers to about 20 nanometers, or about 5 nanometers to about 100 nanometers, or about 5 nanometers to about 90 nanometers, or about 5 nanometers to about 80 nanometers, or about 5 nanometers to about 70 nanometers, or about 5 nanometers to about 60 nanometers, or about 5 nanometers to about 50 nanometers, or about 5 nanometers to about 40 nanometers, or about 5 nanometers to about 30 nanometers, or about 5 nanometers to about 20 nanometers.

In some embodiments, the size distribution of the reverse micelles or micelles may be changed by changing the co-solvent. Not wishing to be bound by theory, using a more polar co-solvent may lead to larger reverse micelles or micelles due to the higher solubility of the co-solvent in the reverse micelles or micelles and due to the higher surface tension at the interface between the reverse micelles or micelles and the hydrocarbon component. The size of reverse micelles or micelles may also change if the co-solvent is modified to result in a different surface tension of the reverse micelles or micelles. For instance, a more polar co-solvent will often reduce the surface tension of micelles resulting in smaller structures.

The micro-emulsion is substantially free of water. The presence of water in the micro-emulsion is undesirable because it is not typically compatible with halometallate ionic liquids. Water reacts with the ionic liquid resulting in facile hydrolysis of the halometallate anion. In cases where the ionic liquid is Lewis acidic, this causes reduction in or neutralization of Lewis acidity. By substantially free of water, we mean that the reverse micelles or micelles themselves are not water, and the components in the micro-emulsion do not contain enough water to substantially affect the halometallate anion (i.e., it does not result in appreciable loss of activity for reactions that are catalyzed by the ionic liquid). There is typically less than about 300 wppm water in the micro-emulsion, or less than about 250 wppm water, or less than about 200 wppm water, or less than about 150 wppm water, or less than about 100 wppm water, or less than about 75 wppm water, or less than about 50 wppm water, or less than about 25 wppm water, or less than about 20 wppm water, or less than about 15 wppm water, or less than about 10 wppm water, or less than about 5 wppm water, or less than about 1 wppm water.

The ionic liquid comprises a cation and an anion. The cation is generally a nitrogen, phosphorous, or sulfur-based organic cation. In some embodiments, the cation is amphiphilic in nature and at least slightly soluble in the co-solvent. By "slightly soluble" we mean the cation is soluble in an amount of at least 0.5 mole ppm in the co-solvent. If the cation and anion are both not amphiphilic, an additional surfactant may be needed. In many cases, the ionic liquid is fully miscible with the co-solvent.

Suitable cations include, but are not limited to, nitrogen-based organic cations, phosphorus based organic cations, sulfur based cations, or combinations thereof. Examples of cations include tetraalkyl phosphoniums, dialkylimidazoliums, alkylimidazoliums, pyridiniums, alkyl pyridiniums, dialkyl pyridiniums, alkylpyrrolidiniums, dialkylpyrrolidiniums, trialkylammoniums, tetraalkylammoniums, lactamiums, alkyl-lactamiums and trialkylsulfoniums. Mixtures of cations may be used as well. Examples of suitable cations include, but are not limited to:

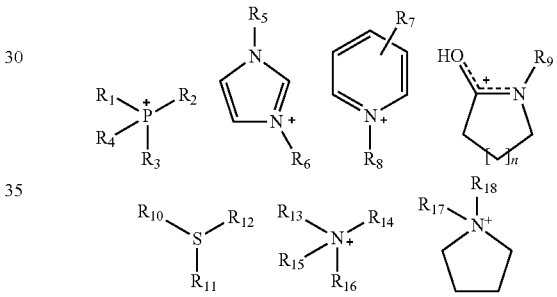

where $R_1$-$R_3$ are independently selected from alkyl groups, alkene groups, naphthene groups, and aryl groups having 1 to 12 carbon atoms, and R4 is independently selected from alkyl groups, alkene groups, naphthene groups, and aryl groups having 1 to 15 carbon atoms; and where $R_5$-$R_{18}$ are independently selected from hydrogen, alkyl groups, alkene groups, naphthene groups, and aryl groups having 1 to 20 carbon atoms, n is 1 to 8, and the alkyl, naphthene, alkene and aryl groups may be substituted with halogens, or other alkyl, aryl and naphthene groups.

In some embodiments, the anion is a halometallate or anion with acidic character, and in most embodiments, with Lewis acidic character. In other embodiments, it can be neutral or basic in character. Halometallate anions may contain a metal selected from Al, Sc, Ti, V, Cr, Mn, Fe, Co, Ni, Cu, Zn, Ga, Y, Zr, Nb, Mo, In, Sn, Sb, La, Ce, Hf, Ta, W, or combinations thereof, and a halide selected from F, Cl, Br, I, or combination thereof. The halometallate may be a simple halometallate or a composite in which more than one metal is used. For catalytic applications requiring Lewis acidity (such as alkylation, disproportionation, reverse disproportionation, oligomerization, and isomerization), the ratio of moles of halide to moles of metal in the anion is less than 4. The anion may be formally an anion, or it may be an anion associated with a metal halide. For instance, the anion may be $AlCl_4^-$ associated with $AlCl_3$. In some embodiments, such as those where the ionic liquid comprises an imidazolium based cation, the ratio of moles of halide to moles of metal in the anion must be less than 4 in order for a micro-emulsion to form.

In embodiments in which the micro-emulsion contains reverse micelles, the hydrocarbon component is continuous and the ionic liquid component comprises reverse micelles that are dispersed in the hydrocarbon component. A majority of the hydrocarbon is in the hydrocarbon component. The co-solvent may be in the hydrocarbon component, the ionic liquid component, or both. In embodiments in which the micro-emulsion contains micelles, the hydrocarbon component forms the core of micellular structures which are surrounded by the ionic liquid component and optional surfactant. The micelles are dispersed in a continuous medium comprising the co-solvent.

The hydrocarbon comprises at least a part of the less polar hydrocarbon component of the micro-emulsion. A majority of the hydrocarbon is contained in the hydrocarbon component. The hydrocarbon may be a paraffin, an olefin, an aromatic, a naphthene, or mixtures of these. When micro-emulsions containing ionic liquid are used to catalyze a hydrocarbon conversion process, the hydrocarbon reactants also serve as a portion of the hydrocarbon component.

In order to form a micro-emulsion containing reverse micelles, there must be at least some solubility of the amphiphile in both the hydrocarbon component and the ionic liquid component of the micro-emulsion. Here, at least some solubility of the amphiphile in the hydrocarbon component is defined as the amphiphile being soluble in an amount of at least 0.5 mole ppm in the hydrocarbon component. If the cation and anion are both not amphiphilic, an additional surfactant may be needed to act as the amphiphile. The solubility of the ionic liquid or the optional surfactant in the ionic liquid component is generally much higher than in the hydrocarbon component and depends on the type of ionic liquid or the optional surfactant and size of the reverse micelles.

In cases where a non-polar hydrocarbon medium is desired (for instance, in motor fuel alkylation where the medium must contain isobutane), a co-solvent is used to modify the polarity of the hydrocarbon. The co-solvent is more polar than the hydrocarbon. The co-solvent must also be compatible with the ionic liquid and must be miscible with the hydrocarbon. Here, miscible with the hydrocarbon means that the co-solvent is soluble in an amount of at least 1 mol % in the hydrocarbon. Suitable co-solvents are any organic solvents containing at least one atom that is not carbon or hydrogen. Examples include, but are not limited to, halomethanes, other halogenated hydrocarbons, halocarbons, halogenated aromatics, or combinations thereof. Halogenated hydrocarbons are any compounds that contain carbon, hydrogen, and a halogen atom or atoms. Halomethanes are any compounds of the formula $CH_{4-n}X_n$ where X is selected from F, Cl, Br, I, or a combination thereof. Halocarbons are any compounds that contain only carbon and one or more halogens. Halogenated aromatics are aromatic compounds containing one or more halogen atoms, such as chlorobenzene. Halomethanes, halocarbons, halogenated aromatics, and compounds with no hydrogen attached to the adjacent (beta) carbon atom are preferable to compounds with a beta hydrogen (such as halogenated hydrocarbons with more than one carbon) because of the potential to eliminate a halogen and a hydrogen to form a hydrogen halide and an olefin. Suitable co-solvents include, but are not limited to, chloroform, dichloromethane, chloromethane, chlorobenzene, dichlorobenzene, fluoromethane, difluoromethane, trifluoromethane, and 1-chloro-2,2-dimethylpropane.

In cases where the ionic liquid is not Lewis acidic or where a weaker Lewis acid is utilized, other co-solvents may be used that would otherwise be reactive with stronger Lewis acids. These include, but are not limited to, ethers (e.g., tetrahydrofuran, and diethyl ether), alcohols (e.g., butanol, propanol, and methanol), amides (e.g., dimethylformamide, and dimethylacetamide), esters (e.g., ethyl acetate), ketones (e.g., acetone), nitriles (e.g., acetonitrile), sulfoxides (e.g., dimethylsulfoxide), sulfones (e.g., sulfolane), or combinations thereof.

In some embodiments, the viscosity of the co-solvent is less than about 1 centipoise at 25° C. Preferably, the viscosity of the co-solvent is less than about 0.6 centipoise at 25° C. This may be advantageous if the micro-emulsion is used in a process, such as alkylation, for which high viscosity may not be desirable.

In some embodiments, no additional surfactant is needed because the ionic liquid itself acts as an amphiphile to make a stable micro-emulsion. However, if a non-amphiphilic ionic liquid is used or if the use of less co-solvent is desired, a surfactant may be added. The surfactant can be cationic, anionic, or neutral. The surfactant can be amphiphilic and non-protic (i.e., it does not contain an acidic H atom bound to N, O, or S). Protic surfactants with very weakly acidic protons such as ternary ammonium salts and cyclic amides may also be suitable. Many surfactants that are not reactive with the ionic liquid are suitable. Examples of classes of such surfactants include, but are not limited to, surfactants containing functional groups such as amphiphilic quaternary ammonium salts, ternary ammonium salts, phosphonium salts, sulfonate salts, phosphonate salts, di-substituted amides (e.g., amides of the formula R—(C=O)—NR$_2$, where R groups are generally alkyl or aryl groups but may be substituted as well), ethers, or glymes. Ideally, the anion of the quaternary ammonium salt, the ternary ammonium salt, or the phosphonium salt may be selected to match the anion of the ionic liquid or selected to be compatible with it. By compatible with the anion of the ionic liquid we mean that the anion of the additional surfactant does not neutralize the Lewis acidity of the ionic liquid anion or co-ordinate strongly to the ionic liquid anion such that the catalyst activity is substantially decreased. By substantially decreased we mean that the reaction rate for isobutane alkylation with olefins is decreased by more than 25% for a mole ratio of surfactant to ionic liquid of 1:1 compared to the same conditions with no additional surfactant. As an example of compatible surfactant anions, Cl$^-$, AlCl$_4^-$ or Al$_2$Cl$_7^-$ may be used as the anion with an Al$_2$Cl$_7^-$ ionic liquid (as may the bromide versions). Examples of cationic quaternary ammonium salts are cetyltrimethylammonium chloride, and benzyldimethyltetradecylammonium chloride. Anionic surfactants may also be suitable; however, most include sulfonate groups which are expected to be reactive with, or coordinate to, a Lewis acidic ionic liquid. Ideally, the cation of the sulfonate salt or phosphonate salt may be selected to match the cation of the ionic liquid or selected to be compatible with the cation of the ionic liquid. For instance, if the acidic ionic liquid is tributylhexylphosphonium heptachloroaluminate the surfactant could be tributylhexylphosphonium dodecyl sulfonate. As demonstrated below, the use of a surfactant allows use of a smaller quantity of polar co-solvent, and in some cases results in larger reverse micelles.

Another optional material is a catalyst promoter. In many hydrocarbon conversion reactions, such as motor fuel alkylation and paraffin disproportionation, a Brønsted acidic catalyst promoter is needed. Two common classes of promoters are anhydrous hydrogen halides (for instance, HCl) and halogenated hydrocarbons (such as 2-chlorobutane or 2-chloro-2-methyl propane (t-butyl chloride)). The halogenated hydrocarbons react in the presence of a Lewis acid to form a hydrogen halide and an olefin.

The above materials are mixed in specific ratios such as to stabilize ionic liquid micro-emulsions. The ionic liquid is typically present in an amount of about 0.05 wt % to about 40 wt % of the micro-emulsion, or about 0.05 wt % to about 35 wt %, or about 0.05 wt % to about 30 wt %, or about 0.05 wt % to about 25 wt %, or about 0.05 wt % to about 20 wt %, or about 0.05 wt % to about 15 wt %, or about 0.05 wt % to about 10 wt %, or about 0.05 wt % to about 5 wt %, or about 0.05 wt % to about 1 wt %.

The co-solvent is typically present in an amount of about 30 wt % to about 80 wt % of the micro-emulsion, or about 40 wt % to about 80 wt %, or about 30 wt % to about 70 wt %, or about 30 wt % to about 60 wt %, or about 40 wt % to about 70 wt %.

The amount of co-solvent needed is lower when less ionic liquid is present in the composition. The molar ratio of the surfactant to the ionic liquid is typically less than about 2.5:1, or less than about 1.5:1.

When the catalyst promoter is present, the molar ratio of the catalyst promoter to the ionic liquid is typically about 0.1:1 to about 1:1, or about 0.1:1 to about 0.7:1, or about 0.2:1 to about 0.7:1.

The amounts of co-solvent and surfactant needed to stabilize the micro-emulsion depend on the amount of ionic liquid and hydrocarbon component present. When surfactant is included in the micro-emulsion, generally less co-solvent is needed. When more ionic liquid is included in the micro-emulsion, generally more surfactant or more co-solvent is needed.

The amounts of each material needed to result in a stable micro-emulsion may be determined by determination of a phase diagram. The phase diagram for a given combination of hydrocarbon, co-solvent, ionic liquid, optional surfactant and catalyst promoter is constructed by preparing mixtures containing various known amounts of the materials. A particular composition is then determined to be a micro-emulsion or consist of two distinct phases. Determination of whether a composition is a micro-emulsion or two distinct phases is generally completed by assessing turbidity of the mixture or identifying an interface between two phases, but may be accomplished by other means known in the art such as dynamic light scattering, conductivity measurement, or x-ray scattering. A mixture which is a micro-emulsion is then subjected to addition of the hydrocarbon or ionic liquid to determine the composition at which the phase boundary between micro-emulsion and two-phase composition exists. Alternatively, a mixture which is two phases is subjected to addition of co-solvent or surfactant to determine the composition at which the phase boundary between micro-emulsion and two-phase composition exists.

The micro-emulsion can be formed by contacting or otherwise mixing the hydrocarbon, the co-solvent, the ionic liquid, the optional surfactant, and the optional catalyst promoter. The hydrocarbon has a polarity less than the polarity of the co-solvent. In some embodiments, the co-solvent is miscible in the hydrocarbon, at least up to the desired composition. The ionic liquid comprises a halometallate anion and a cation. In some embodiments, the ionic liquid is at least slightly soluble in the co-solvent. By slightly soluble, we mean that at least 1 wt % of the ionic liquid is soluble in the co-solvent. The ionic liquid is present in an amount of about 0.05 wt % to about 40 wt % of the micro-emulsion.

The materials can be combined in different ways. For example, the hydrocarbon and co-solvent can be combined first, and then combined with ionic liquid. Alternatively, the ionic liquid and the co-solvent can be combined first, and then combined with the hydrocarbon. The optional surfactant and optional catalyst promoter can be added at different times and to different combinations of the materials. For example, the catalyst promoter and optional surfactant can be added to the hydrocarbon, the co-solvent, the ionic liquid, or any combinations of these materials. In another alternative, all of the materials could be combined at the same time. Other ways of combining the materials would be understood by those skilled in the art.

In one method, an ionic liquid and an optional surfactant are dissolved in a co-solvent to form the ionic liquid component. The ionic liquid comprises a halometallate anion and a cation. The ionic liquid component is introduced into a hydrocarbon to form the micro-emulsion. The polarity of the hydrocarbon is less than the polarity of the co-solvent, and the co-solvent is miscible in the hydrocarbon. The hydrocarbon component comprises the hydrocarbon and the co-solvent. The ionic liquid is present in an amount of about 0.05 wt % to about 40 wt % of the micro-emulsion. If a catalyst promoter is included, it can be added to the ionic liquid component, the hydrocarbon, the co-solvent, or the micro-emulsion.

Another method involves mixing the hydrocarbon with a co-solvent to form a hydrocarbon component. The polarity of the hydrocarbon is less than the polarity of the co-solvent, and the co-solvent is miscible in the hydrocarbon. The ionic liquid and an optional surfactant are added to the hydrocarbon component to form the micro-emulsion. The ionic liquid is present in an amount of about 0.05 wt % to about 40 wt % of the micro-emulsion. If a catalyst promoter is included, it can be added to the hydrocarbon, the co-solvent, the ionic liquid, or the micro-emulsion.

Processes using ionic liquid micro-emulsions are described in U.S. Application No. 62/141,056; U.S. Application No. 62/141,070; and U.S. Application No. 62/141,076, all filed on Mar. 31, 2015, each of which is incorporated herein by reference.

The need for high surface area in order to increase the reaction rate and the selectivity of the catalyst is met by the very small size of the reverse micelles or other polar structures in the micro-emulsion. Furthermore, because the ionic liquid itself may act as the amphiphile, the catalyst may be concentrated on the surface of the reverse micelles or other polar structures in the micro-emulsion. Consequently, diffusion of the reactants from the bulk hydrocarbon phase into the interior of the droplets may not be necessary. This provides additional reduction in mass transfer resistance.

The surface area to volume ratio of the polar structures in the micro-emulsion is much higher than the surface area to volume ratio of ionic liquid droplets generated by shear mixing alone. Significantly less ionic liquid needs to be used in a micro-emulsion to provide the same amount of surface area as in conventional ionic liquid systems. The amount of ionic liquid can be low (e.g., about 0.5% by volume) compared to traditional ionic liquid alkylation reactions (5-10% by volume). The amount of ionic liquid can be adjusted if it is accompanied by a change in the amount of co-solvent in order to stabilize the micro-emulsion or otherwise prevent a second liquid phase from forming.

In addition to advantages for reactivity, the nature of the micro-emulsion may allow catalyst recovery without the specialized equipment typically used in conventional ionic liquid processes. To recover the catalyst, the micro-emulsion is broken by changing the reaction mixture composition such that the micro-emulsion is no longer thermodynamically stable. This can be done by any suitable method, including, but not limited to, removing a portion of the polar co-solvent (for example, by vaporization), increasing the amount of the isoparaffin, increasing the amount of alkylate, adding an additional liquid having a polarity less than the polarity of the co-solvent (including a hydrocarbon), adding ionic liquid, or combinations thereof. Once the micro-emulsion is no longer stable, a second phase of ionic liquid is formed which may be settled by gravity. Other separation process could be used including, but not limited to, sonication, electrostatic precipitation, filtration, adsorption, centrifugal separation, distillation, vaporization, or combinations thereof. These separation processes could be used in addition to gravity separation, or in place of it.

The process can be used for a variety of hydrocarbon conversion processes, including, but not limited to, motor fuel alkylation, paraffin disproportionation, paraffin reverse di sproportionation, paraffin isomerization, aromatic alkylation, cracking, olefin oligomerization or polymerization. It can also be used for separation, such as contaminant removal processes, or bulk separation processes. One type of separation process is an extraction process.

In motor fuel alkylation, an isoparaffin having from 4 to 10 carbon atoms is reacted with an olefin having from 2 to 8 carbon atoms, or 3 to 5 carbon atoms, to form an alkylate. In paraffin disproportion, a paraffin having from at least 3 to about 50 carbon atoms reacts to form products having one more carbon and one less carbon than the starting paraffin. In paraffin reverse disproportionation, two paraffins having different carbons numbers are reacted to form other paraffins having carbon numbers between those of the initial reactants. In paraffin isomerization, a paraffin having at least 4 to about 50 carbon atoms is isomerized to a different configuration having the same number of carbon atoms, e.g., normal butane to isobutane. In aromatic alkylation, an olefin having at least 2 to about 20 carbon atoms is reacted with an aromatic compound to form an alkylated aromatic, e.g. propylene with benzene to form cumene. Cracking involves one component forming two smaller components, e.g., an olefin reacting to form two olefins, or an alkylaromatic reacting to form an olefin and an aromatic. Olefin oligomerization and polymerization involve reacting olefins with each other to form a product with increased molecular weight. Separation processes include contaminant removal processes and bulk separations. Contaminant removal processes involve contacting a hydrocarbon stream containing one or more contaminants, such as compounds containing sulfur or nitrogen, with the micro-emulsion to remove the contaminants from the hydrocarbon stream. Bulk separation processes involve contacting a mixed hydrocarbon stream with the micro-emulsion to increase the concentration of a specific hydrocarbon or group of hydrocarbons in the hydrocarbon stream. Bulk separation processes include but are not limited to paraffin/olefin separation and aromatic/non-aromatic separation.

Although the following description focuses on motor fuel alkylation, those skilled in the art will recognize that the process is applicable to other hydrocarbon conversion process or separation processes.

The reaction takes place using a micro-emulsion comprising a polar phase comprising ionic liquid and an oil phase comprising a hydrocarbon component and a co-solvent. In some embodiments, the micro-emulsion comprises reverse micelles suspended in the oil phase.

The micro-emulsion is introduced into the reaction zone (or is formed there), along with the other reaction components. For example, in an alkylation process, a micro-emulsion is formed from an isoparaffin, a co-solvent, an ionic liquid, and optionally a surfactant and/or a catalyst promoter. An olefin is introduced into the reaction zone where it reacts with the isoparaffin to form alkylate.

After the reaction, the micro-emulsion is broken resulting in two distinct liquid phases. One phase is an ionic liquid phase that contains a majority of the ionic liquid. The other phase is a hydrocarbon phase that contains a majority of the hydrocarbon which can include alkylate, unreacted isoparaffin, and unreacted olefin (if present). Both phases may contain co-solvent, surfactant (if present) and catalyst promoter (if present). The hydrocarbon phase may contain a minor portion of the ionic liquid, and the ionic liquid phase may contain a minor component of the hydrocarbons.

The ionic liquid phase is separated from the hydrocarbon phase. This separation typically takes place by gravity due to the density difference between the ionic liquid phase and the hydrocarbon phase and/or using one of the other processes discussed above. The ionic liquid phase can be recycled to the reaction zone. Separation of the components of the ionic liquid phase may be desirable prior to recycling one or more of the components of the ionic liquid phase to the reaction zone. Such separation may take place by distillation, vaporization, or other means of separation known to those skilled in the art.

The components of the hydrocarbon phase can be separated using a suitable separation process. The alkylate can be recovered. Any unreacted isoparaffin, unreacted olefin, surfactant, or catalyst promoter can be recovered, processed, and/or recycled. Suitable separation and recovery processes are well known.

The process can be a batch, semi-batch, or continuous process. The reaction and separation can take place in a single vessel or in multiple vessels.

Typical alkylation reaction conditions include a temperature in the range of about $-100°$ C. to about $100°$ C., or about $-50°$ C. to about $70°$ C., or about $-10°$ C. to about $70°$ C., or about $0°$ C. to about $70°$ C., or about $0°$ C. to about $60°$ C., or about $0°$ C. to about $50°$ C., or about $20°$ C. to about $60°$ C., or about $20°$ C. to about $50°$ C. It is desirable that the ionic liquid, co-solvent, and isoparaffin maintain their liquid states through the operating temperature range.

The pressure is typically in the range of 0.001 MPa to about 8.0 MPa, or about 0.002 MPa to about 5 MPa. The pressure is preferably sufficient to keep the reactants in the liquid phase. Vacuum pressures may be desirable if vaporization of the co-solvent is used to remove heat and the process is at low temperature.

The residence time of the reactants in the reaction zone is in the range of a few seconds to several hours, or about 0.5 min to about 4 hours, or about 2 min to about 120 min or about 2 min to about 60 min.

The overall molar ratio between the isoparaffin and olefin feeds is in the range of about 1:1 to about 100:1, or about 5:1 to about 100:1, or about 5:1 to about 70:1, or about 5:1 to about 25:1, or about 5:1 to about 20:1, or about 5:1 to about 15:1. The overall molar ratio is defined as the ratio of the total amount of isoparaffins entering the reaction zone or present in the reaction zone at the start of the reaction to the total amount of olefins entering the reaction zone or present in the reaction zone at the start of the reaction. Both isoparaffins and olefins may enter the reaction zone in one location or several locations, and may be present in the reaction zone at the start of the reaction.

Figure 5:
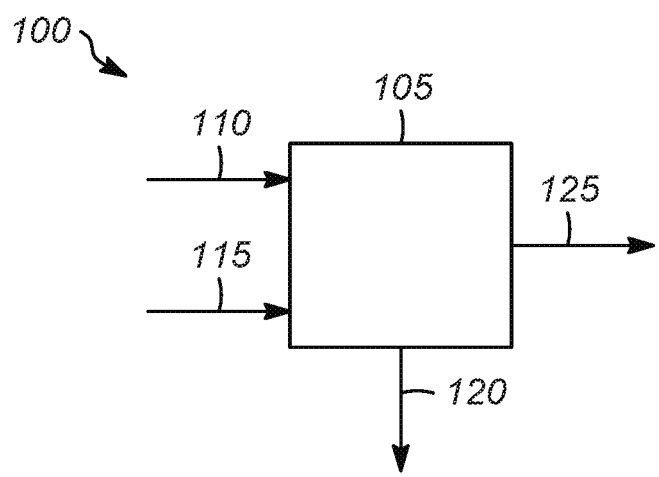
FIG. 5 is one embodiment of a process of the present invention.

FIG. 5 illustrates an embodiment of an alkylation process 100 in which the reaction and separation processes occur in a single process zone 105. The micro-emulsion 110 is fed into the zone process 105. Alternatively, the components to form the micro-emulsion could be fed into the zone, and the micro-emulsion could be formed in the process zone 105. The olefin 115 is fed into the process zone 105 where the reaction takes place forming the alkylate. The reaction mixture will contain a mixture of ionic liquid, alkylate, unreacted isoparaffin, unreacted olefin (if present), co-solvent, surfactant (if present), and catalyst promoter (if present).

The composition of the reaction mixture is altered to destroy the micro-emulsion. This can be done in a variety of ways. A portion of the co-solvent could be removed, for example by changing the pressure in the reactor to vaporize the co-solvent. Another way to change the composition is to add one or more of isoparaffin, alkylate, an additional liquid that has a polarity less than the polarity of the co-solvent (e.g., a hydrocarbon), or an ionic liquid. Any of these will change the composition of the reaction mixture so that the micro-emulsion is no longer stable. The ionic liquid will then separate from the remaining components.

The ionic liquid will settle out of the remaining components due to the density differences. Ionic liquid stream 120, which may contain some other components such as a portion of the co-solvent, can be removed from the process zone 105. The ionic liquid stream 120 can be recycled for further use (not shown), if desired. All or a portion of the ionic liquid stream 120 can be further processed as needed before recycle, including but not limited to, regeneration of the ionic liquid, or recovery of co-solvent. The remaining reaction mixture 125 can be removed and sent for further processing (not shown) including, but not limited to separation of the remaining mixture into its various components and the recovery and/or recycle of the components.

Figure 6:
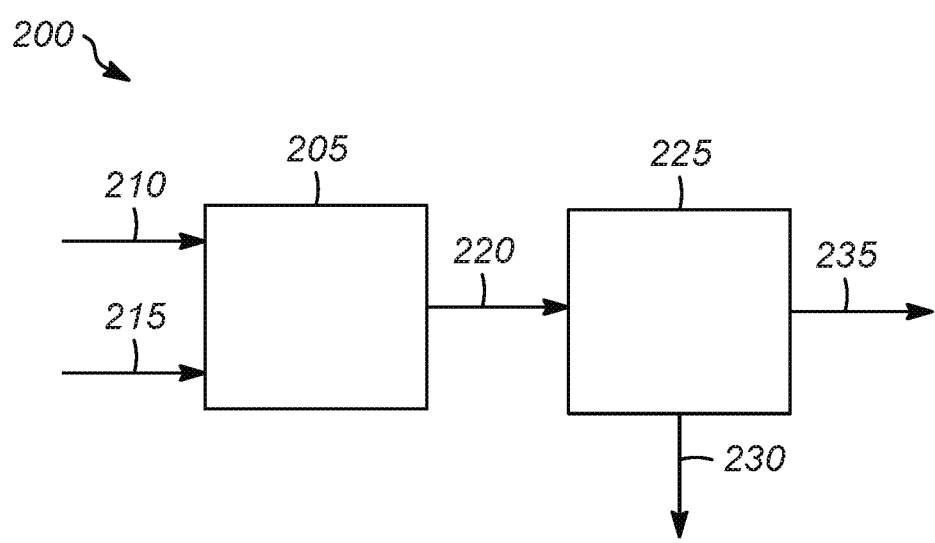
FIG. 6 is another embodiment of a process of the present invention.

FIG. 6 illustrates another embodiment of an alkylation process 200 in which the reaction and separation take place in different zones. The micro-emulsion (or the components to form the micro-emulsion) 210 is fed into the reaction zone 205. The olefin 215 is fed into the reaction zone 205, and the alkylate is formed.

The reaction mixture 220, which contains the mixture of ionic liquid, alkylate, unreacted isoparaffin, unreacted olefin (if present), co-solvent, surfactant (if present), and catalyst promoter (if present), is sent to a separation zone 225. The composition of the reaction mixture 220 is changed so that the micro-emulsion is destroyed and the ionic liquid separates from the majority of the remaining components. Ionic liquid stream 230, which may contain some other components such as a portion of the co-solvent, can be removed from the separation zone 225 for further processing. The remaining reaction mixture 235 can also be removed for further processing.

The reaction rate and selectivity may be changed by changing the amounts of the components in the micro-emulsion. For example, if the co-solvent is more viscous than the isoparaffin, increasing the ratio of isoparaffin to co-solvent would decrease the viscosity of the oil phase, which would result in faster mass transfer. Higher isoparaffin to co-solvent ratio would also increase the concentration of isoparaffin. With higher concentration of isoparaffin, selectivity to the desired alkylate product rather than oligomer would improve. Adding a second co-solvent with a lower viscosity or using a different co-solvent with a lower viscosity may result in a faster reaction if the reaction is mass-transfer limited. Decreasing the size of the polar structures such as reverse micelles in the micro-emulsion may result in faster reaction. Decreasing the size of polar structures in the micro-emulsion may be accomplished by changing the composition (for instance by changing the amount of co-solvent or surfactant), or mixing with higher shear to improve contacting.

Although reverse micelles or other polar structures in the micro-emulsion are generated due to their thermodynamic stability rather than by shear mixing, adequate mixing is necessary to insure a homogenous mixture and uniform concentration profiles. This mixing facilitates mass transfer in the micro-emulsion and prevents local in-homogeneities in which the micro-emulsion is not stable. The shear rate is defined as the tip speed of the mixing element (such as an impeller) divided by the distance to the nearest surface (such as a baffle or vessel wall). See e.g., U.S. Pat. No. 8,163,856 examples 1-3. In some embodiments, the shear rate is greater than about 300 inverse seconds, or greater than about 350 inverse seconds, or greater than about 400 inverse seconds, or greater than about 425 inverse seconds.

The amount of olefin reacted in moles olefin reacted per mole of ionic liquid is calculated by dividing the total amount of olefin converted in the reaction zone by the total amount of ionic liquid in the reaction zone (or which flowed through the reaction zone). In batch or semi-batch reactions, the amount of moles of olefin converted per mole of ionic liquid is an indication of how much olefin can be converted before catalyst deactivation.

The rate of olefin reaction is calculated by dividing the total amount of olefin converted in the reaction zone per unit time (in hours) divided by the amount of ionic liquid in the reaction zone. In some embodiments, the rate of olefin reaction is greater than about 20 mole olefin/mole ionic liquid/hour, or greater than about 30 mole olefin/mole ionic liquid/hour, or greater than about 40 mole olefin/mole ionic liquid/hour, or greater than about 50 mole olefin/mole ionic liquid/hour, or greater than about 60 mole olefin/mole ionic liquid/hour, or about 20 mole olefin/mole ionic liquid/hour to about 300 mole olefin/mole ionic liquid/hour, or about 20 mole olefin/mole ionic liquid/hour to about 200 mole olefin/mole ionic liquid/hour, or about 20 mole olefin/mole ionic liquid/hour to about 100 mole olefin/mole ionic liquid/hour, or about 20 mole olefin/mole ionic liquid/hour to about 80 mole olefin/mole ionic liquid/hour, or about 30 mole olefin/mole ionic liquid/hour to about 70 mole olefin/mole ionic liquid/hour.

The selectivity to a particular product or group of products is defined as the amount of the particular product or group of products in weight percent, divided by the amount of products containing a number of carbon atoms greater than the number of carbon atoms in one isoparaffin reactant in weight percent. For example for the alkylation of isobutane and butene, the selectivity for $C_8$ hydrocarbons is the wt % of hydrocarbons containing exactly 8 carbon atoms in the product divided by the wt % of all products containing 5 or more carbon atoms. Similarly, the selectivity to $C_5$-$C_7$ hydrocarbons is the wt % of hydrocarbons containing exactly 5, 6 or 7 carbon atoms in the product divided by the wt % of all products containing 5 or more carbon atoms, and the selectivity to $C_9$+ hydrocarbons is the wt % of hydrocarbons containing 9 or more carbon atoms in the product divided by the wt % of all products containing 5 or more carbon atoms.

In some embodiments, the selectivity to primary alkylation products is greater than about 50 wt %. Here, primary alkylation products are defined as products containing the number of carbon atoms equal to the sum of the number of carbon atoms in one isoparaffin reactant plus the number of carbon atoms in one olefin reactant. The selectivity to primary alkylation products is defined as the amount of primary alkylation products in weight percent, divided by the amount of products containing a number of carbon atoms greater than the number of carbon atoms in one isoparaffin reactant in weight percent. For example, for the alkylation of isobutane and butene, the selectivity for $C_8$ hydrocarbons could be greater than about 50 wt % of the $C_{5+}$ hydrocarbons. Without being bound by theory, selectivity to $C_8$ hydrocarbons is higher, and selectivity to $C_5$-$C_7$ hydrocarbons is lower if the olefin feed rate is slower, if the isoparaffin/olefin ratio is higher, if residence time is longer, if temperature is lower, or if a less hydrophobic ionic liquid is used (e.g., tributylmethylphosphonium instead of tributylhexylphosphonium). $C_8$ selectivity is probably higher if less co-solvent and more isoparaffin is used. Selectivity may be higher if a less viscous co-solvent is used due to improved mass transfer. Reaction may be faster (conversion is higher for similar conditions) if more promoter or ionic liquid is used, if the co-solvent is less viscous, or if more shear is imparted.

The micro-emulsion includes an oil phase and polar structures such as reverse micelles. The micro-emulsion is formed from an ionic liquid, a hydrocarbon phase, and a co-solvent. The micro-emulsion may optionally contain an additional surfactant and/or a catalyst promoter.

The reverse micelles or other polar structures will primarily contain ionic liquid. However, in some cases, some isoparaffin and/or co-solvent may be present in the reverse micelles or other polar structures.

EXAMPLES

Example 1

In the examples below, n-hexane is used as the hydrocarbon, tributylhexylphosphonium heptachloroaluminate is used as the ionic liquid, and dichloromethane is used as the co-solvent.

Micro-emulsions were generated by preparing a mixture of ionic liquid and (in some cases) benzyldimethyltetradecylammonium chloride, referred to as "surfactant" below. Four different compositions were prepared with the following surfactant:ionic liquid mole ratios. Formulation 1 had a molar ratio of surfactant:ionic liquid of 2.1:1. Formulation 2 had a molar ratio of surfactant:ionic liquid of 1.7:1. Formulation 3 had a molar ratio of surfactant:ionic liquid of 0.83:1. Formulation 4 had no surfactant. Sufficient dichloromethane was added to dissolve the ionic liquid and surfactant. Following this, n-hexane was added dropwise, with shaking. When turbidity appeared, this composition was recorded as the boundary between the micro-emulsion region and the two-phase region of the phase diagram. A drop or drops of dichloromethane was then added to check that cloudiness disappeared. This was recorded as a second limit for the phase boundary. Additional dichloromethane was added, and the procedure was repeated. As the ionic liquid and surfactant became more dilute in the mixture, less dichloromethane was needed in the mixture to clarify the liquid. When a large amount of surfactant was added to the ionic liquid, less dichloromethane was needed to stabilize the same amount of ionic liquid. However, with little or no surfactant a phase boundary was also found. A phase diagram showing the required dichloromethane/hexane ratio to form a clear liquid (the phase boundary) for each of the formulations 1-4 as a function of total ionic liquid plus surfactant mole fraction is shown in FIG. 1.

The micro-emulsion region (M-E) is above and to left of the phase boundary while the two phase region (2P) is below and to the right of the phase boundary. Micro-emulsions are broken to produce two phases when the composition is changed from a composition in the micro-emulsion region to the two phase region. A list of compositions measured which were on the phase boundary are in Table 1.

Example 2

Compositions that were sufficiently cloudy and contained sufficient amounts of ionic liquid would eventually settle to form two liquid phases, indicating that cloudiness was due to formation of a second liquid phase. In mixtures that were not cloudy, formation of a micro-emulsion was presumed. This was confirmed by measuring particle size by dynamic light scattering (DLS) using a Zetasizer Nano ZS two angle particle and molecular size analyzer (Malvern Instruments LTD., UK) for two compositions, one with and one without additional surfactant. Compositions were prepared as described in Example 1. A composition was prepared with 2.9 wt % tributylhexylphosphonium heptachloroaluminate ionic liquid, 2.9 wt % benzyldimethyltetradecylammonium chloride, 54.6 wt % dichloromethane and 39.5 wt % hexane. The micro-emulsion was placed in a quartz cuvette (1 cm path length) with a Teflon stopper. Particle size distributions were measured using the analyzer's particle size mode. 30 scans were collected for each sample assuming viscosity of 0.347 centipoise (the volume weighted average viscosity of n-hexane and dichloromethane in the mixture) of the continuous phase, and refractive index of 1.403 (the volume weighted average refractive index of n-hexane and dichloromethane in the mixture). This composition had measured volume normalized average particle size of 12±2 nm. This composition is indicated with a "B" on FIG. 1. Volume normalized particle size distributions for five repeat measurements (1-5) are shown in FIG. 2.

A composition with 6.16 wt % tributylhexylphosphonium heptachloroaluminate ionic liquid, 62.7 wt % dichloromethane and 31.2 wt % hexane had measured particle size of 3±2 nm. This composition is indicated with an "A" on FIG. 1. Volume normalized particle size distributions for four repeat measurements (1-4) are shown in FIG. 3. The size of the particles is more than three orders of magnitude smaller than droplets generated by impellers.

TABLE 1

Compositions on phase boundary between micro-emulsion and two-phase mixture for compositions containing tributylhexylphosphonium heptachloroaluminate as the IL, benzyldimethyltetradecylammonium chloride as the surfactant, dichloromethane and n-hexane

| IL wt % | Surfactant wt % | Dichloromethane wt % | Hexane wt % | Average size by DLS |
|---------|-----------------|----------------------|-------------|---------------------|
| 0.00%   | 2.83%           | 26.5%                | 70.7%       |                     |
| 0.00%   | 2.73%           | 25.6%                | 71.7%       |                     |
| 0.00%   | 2.78%           | 26.0%                | 71.2%       |                     |
| 20.78%  | 0.00%           | 64.9%                | 14.3%       |                     |

TABLE 1-continued

Compositions on phase boundary between micro-emulsion and two-phase mixture for compositions containing tributylhexylphosphonium heptachloroaluminate as the IL, benzyldimethyltetradecylammonium chloride as the surfactant, dichloromethane and n-hexane

| IL wt % | Surfactant wt % | Dichloromethane wt % | Hexane wt % | Average size by DLS |
|---|---|---|---|---|
| 6.27% | 0.00% | 62.0% | 31.7% | |
| 6.16% | 0.00% | 62.7% | 31.2% | 3 nm |
| 12.66% | 0.00% | 60.1% | 27.2% | |
| 4.61% | 0.00% | 60.8% | 34.6% | |
| 1.83% | 0.00% | 59.5% | 38.7% | |
| 0.97% | 0.00% | 57.3% | 41.7% | |
| 0.96% | 0.00% | 57.5% | 41.6% | |
| 0.58% | 0.00% | 55.1% | 44.3% | |
| 0.58% | 0.00% | 55.5% | 43.9% | |
| 0.16% | 0.00% | 47.9% | 52.0% | |
| 0.10% | 0.00% | 43.4% | 56.5% | |
| 0.09% | 0.00% | 44.9% | 55.0% | |
| 13.68% | 6.84% | 62.4% | 17.1% | |
| 13.11% | 6.56% | 59.8% | 20.5% | |
| 5.73% | 2.87% | 62.4% | 29.0% | |
| 5.63% | 2.82% | 61.3% | 30.3% | |
| 7.84% | 9.80% | 53.6% | 28.8% | |
| 7.59% | 9.49% | 55.1% | 27.8% | |
| 7.72% | 9.65% | 54.3% | 28.3% | |
| 3.39% | 4.24% | 52.8% | 39.5% | |
| 3.35% | 4.19% | 53.4% | 39.1% | |
| 3.37% | 4.21% | 53.1% | 39.3% | |
| 2.61% | 3.26% | 52.6% | 41.5% | |
| 2.58% | 3.23% | 53.1% | 41.1% | |
| 1.86% | 2.33% | 52.5% | 43.3% | |
| 1.85% | 2.31% | 52.9% | 42.9% | |
| 1.39% | 1.74% | 52.0% | 44.9% | |
| 1.32% | 1.65% | 52.0% | 45.0% | |
| 1.07% | 1.34% | 51.3% | 46.3% | |
| 1.07% | 1.34% | 51.3% | 46.3% | |
| 1.07% | 1.34% | 51.3% | 46.3% | |
| 0.36% | 0.45% | 45.0% | 54.2% | |
| 0.34% | 0.42% | 45.4% | 53.9% | |
| 0.23% | 0.28% | 42.1% | 57.3% | |
| 0.23% | 0.28% | 42.6% | 56.8% | |
| 0.10% | 0.12% | 36.3% | 63.5% | |
| 0.09% | 0.11% | 34.4% | 65.4% | |
| 0.09% | 0.11% | 35.0% | 64.8% | |
| 2.94% | 2.94% | 54.6% | 39.5% | 12 nm |

Example 3

In the examples below, n-hexane is used as the hydrocarbon, and dichloromethane is used as the co-solvent. Four different ionic liquids were tested: tributylhexylphosphonium-$Al_2Cl_7$ was used in formulation 1, tributylmethylphosphonium-$Al_2Cl_7$ was used in formulation 2, 1-butyl-3-methylimidazolilum-$Al_2Cl_7$ was used in formulation 3 and caprolactamium-$Al_2Cl_7$ was used in formulation 4.

Figure 4:
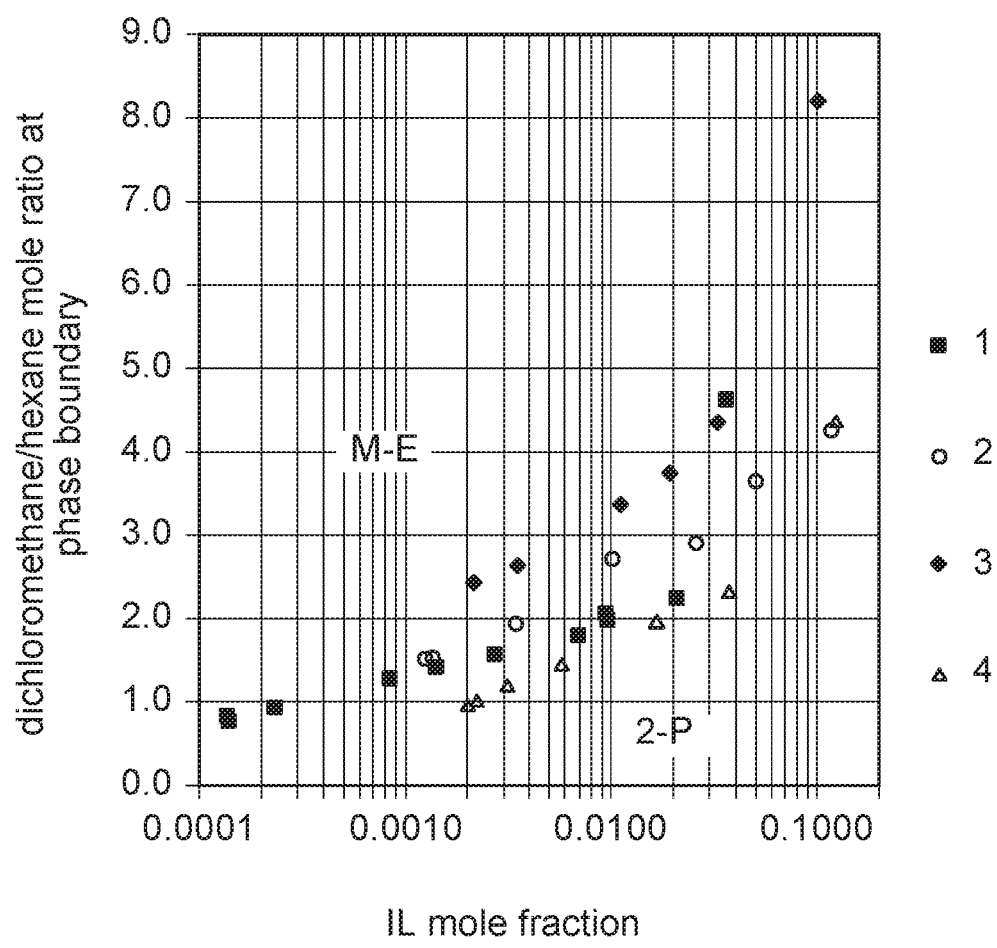
FIG. 4 is a phase diagram showing the dichloromethane/hexane mole ratio as a function of the ionic liquid mole fraction for various ionic liquids.

Micro-emulsions were generated by preparing a mixture of ionic liquid and sufficient dichloromethane to dissolve the ionic liquid and surfactant. Following this, n-hexane was added dropwise, with shaking. When turbidity appeared, this composition was recorded as the boundary between the micro-emulsion region and the two-phase region of the phase diagram. A drop or drops of dichloromethane was then added to check that cloudiness disappeared. This was recorded as a second limit for the phase boundary. Additional dichloromethane was added, and the procedure was repeated. As the ionic liquid became more dilute in the mixture, less dichloromethane was needed in the mixture to clarify the liquid. A phase diagram showing the required dichloromethane/hexane ratio to form a clear liquid (the phase boundary) for each of the formulations 1-4 as a function of total ionic liquid mole fraction is shown in FIG. 4. The micro-emulsion region (M-E) is above and to left of the phase boundary while the two phase region (2P) is below and to the right of the phase boundary. Micro-emulsions are broken to produce two phases when the composition is changed from a composition in the micro-emulsion region to the two phase region. A list of compositions measured which were on the phase boundary are in Table 2.

TABLE 2

Compositions on phase boundary between micro-emulsion and two-phase mixture for compositions containing dichloromethane, hexane and four different ionic liquids.

| | IL wt % | DCM wt % | Hexane wt % | IL mol fraction | DCM/hexane mole fraction |
|---|---|---|---|---|---|
| TBHP-$Al_2Cl_7$ | 21% | 64.94% | 14.29% | 3.65E-02 | 4.61 |
| | 6.3% | 61.99% | 31.73% | 9.60E-03 | 1.98 |
| | 6.2% | 62.68% | 31.16% | 9.41E-03 | 2.04 |
| | 12.7% | 60.13% | 27.22% | 2.05E-02 | 2.24 |
| | 4.6% | 60.83% | 34.56% | 6.95E-03 | 1.79 |
| | 1.8% | 59.49% | 38.68% | 2.70E-03 | 1.56 |
| | 1.0% | 57.32% | 41.72% | 1.41E-03 | 1.39 |
| | 1.0% | 57.46% | 41.58% | 1.41E-03 | 1.40 |
| | 0.6% | 55.09% | 44.33% | 8.50E-04 | 1.26 |
| | 0.578% | 55.50% | 43.92% | 8.42E-04 | 1.28 |
| | 0.159% | 47.87% | 51.97% | 2.31E-04 | 0.93 |
| | 0.096% | 43.45% | 56.45% | 1.39E-04 | 0.78 |
| | 0.093% | 44.90% | 55.01% | 1.36E-04 | 0.83 |
| TBMP-$Al_2Cl_7$ | 45% | 44.53% | 10.63% | 1.18E-01 | 4.25 |
| | 24% | 59.09% | 16.42% | 5.05E-02 | 3.65 |
| | 14% | 63.73% | 22.34% | 2.59E-02 | 2.90 |
| | 6% | 68.44% | 25.67% | 1.02E-02 | 2.71 |
| | 2.0% | 64.20% | 33.75% | 3.43E-03 | 1.93 |
| | 0.8% | 59.67% | 39.51% | 1.36E-03 | 1.53 |
| | 0.8% | 59.49% | 39.76% | 1.24E-03 | 1.52 |
| BMIm-$Al_2Cl_7$ | 36.9% | 56.19% | 6.95% | 1.01E-01 | 8.21 |
| | 14.9% | 68.99% | 16.12% | 3.27E-02 | 4.34 |
| | 9.2% | 71.42% | 19.38% | 1.92E-02 | 3.74 |
| | 5.5% | 72.58% | 21.91% | 1.11E-02 | 3.36 |
| | 5.5% | 72.58% | 21.91% | 1.11E-02 | 3.36 |
| | 1.8% | 70.85% | 27.36% | 3.49E-03 | 2.63 |
| | 1.1% | 69.70% | 29.21% | 2.14E-03 | 2.42 |
| Caprolactamium-$Al_2Cl_7$ | 40.6% | 48.25% | 11.19% | 1.22E-01 | 4.38 |
| | 15.7% | 58.70% | 25.64% | 3.66E-02 | 2.32 |
| | 7.5% | 60.46% | 32.07% | 1.63E-02 | 1.91 |
| | 7.5% | 60.46% | 32.07% | 1.63E-02 | 1.91 |
| | 2.7% | 56.68% | 40.60% | 5.69E-03 | 1.42 |
| | 1.5% | 53.51% | 45.00% | 3.08E-03 | 1.21 |
| | 1.1% | 49.66% | 49.28% | 2.19E-03 | 1.02 |
| | 0.9% | 48.32% | 50.73% | 1.96E-03 | 0.97 |

Example 4

Alkylation

Alkylation of isobutane with 2-butenes was demonstrated using mixtures containing ionic liquid reverse micelles stabilized with a co-solvent. A mixture of mostly branched $C_{5+}$ hydrocarbons was obtained as the product.

Reverse micelles comprising tributylhexylphosphonium heptachloroaluminate (TBHP-$Al_2Cl_7$) ionic liquid were generated by charging a mixture of 0.5 g ionic liquid, 77 g dichloromethane as the co-solvent, and about 60 g of isobutane as the hydrocarbon component into a 300 cc autoclave, equipped with a 1-⅜" pitched blade turbine impeller. Separate experiments using ionic liquid, dichloromethane, and n-hexane show that similar mixtures contain reverse micelles of ionic liquid. Except in Example 2, 2-chlorobutane was used to increase acidity in amounts indicated in Table 1. Here, 2-chlorobutane breaks down to form HCl.

The vessel was pressurized with nitrogen to 3.4 MPa(g) (500 psig). A mixture of cis- and trans-2-butene with about 8 wt % n-pentane (used as a tracer) was added continuously at room temperature while mixing with a pitched-blade impeller. Since reverse micelles are not expected to settle, these reactions were then chemically quenched by adding 20 g of 25 wt % 1-butanol in hexane. The mixture was analyzed by GC under pressure. Butenes conversion was calculated based on the n-pentane tracer. Selectivities are reported as a weight percent of the $C_{5+}$ product. Results are shown in Table 1.

The percent olefin (butene) conversion is defined as (the amount of olefin added to the reactor minus the amount of olefin remaining after the reaction (or at the reactor outlet)) divided by the total amount of olefin added to the reactor times 100.

Comparative Example 5

39 g n-hexane was used instead of dichloromethane. Without dichloromethane, reverse micelles did not form. Rather, the ionic liquid formed a separate liquid phase. The amount of n-hexane used was an equivalent volume to 77 g of dichloromethane used in the other experiments. 0.94 g of olefin was fed over 15 minutes. The isobutane to butene (I/O) ratio was 63.8. The olefin conversion was 17.8% with 16.4% selectivity to $C_8$ products, 2.96% selectivity to heavies ($C_{9+}$) and 80.7% selectivity to light-ends ($C_5$-$C_7$). The ratio between trimethylpentanes and dimethylhexanes (TMP/DMH) was 5.02, and the calculated research octane number (RONC) was 80.1.

Example 5

The general procedure above was used (including dichloromethane to generate reverse micelles) and 0.94 g of olefin was fed over 15 minutes. The isobutane to butene (I/O) ratio was 64.9. The olefin conversion was 44.7% with 25.1% selectivity to $C_8$ products, 9.27% selectivity to heavies ($C_{9+}$) and 65.7% selectivity to light ends ($C_5$-$C_7$). The TMP/DMH ratio was 9.27, and the RONC was 85.8. The reaction rate and selectivities in this example were improved relative to the comparative example with the same ionic liquid loading but without a co-solvent to stabilize reverse micelles.

Example 6

A lower final I/O ratio of 36.8 was used compared to Example 5. 1.63 g of butenes was fed over the course of 15 minutes. Conversion was slightly lower, and the selectivities were slightly worse than in Example 1, although the TMP/DMH ratio and RONC were higher. The olefin conversion was 34.4% with 21.6% selectivity to $C_8$ products, 10.3% selectivity to heavies (C9+) and 68.1% selectivity to light ends ($C_5$-$C_7$). The TMP/DMH ratio was 10.51, and the RONC was 87.8.

Example 7

A much lower I/O ratio of 11.3 was targeted. The olefin feed rate was also reduced. 5.51 g of butenes was fed over the course of 182 minutes. The lower olefin feed rate resulted in higher olefin conversion of 79.0%, lower selectivity to light-end products (23.2%), higher RONC (90.4), and higher TMPP/DMF ratio of 14.9, compared to examples 5 and 6. However, selectivity to heavies ($C_{9+}$) was higher (25.1%).

Example 8

The same conditions were used as in Example 5, but tributylmethylphosphonium heptachloroaluminate was used as the ionic liquid instead of tributylhexylphosphonium (on an equal weight basis). The conversion was much higher than in Example 1 (90.2%), as were the $C_8$ selectivity (60.4%), RONC (94.0), and the TMP/DMH ratio (26.5). The selectivity to heavies ($C_{9+}$) was very low (2.7%) and selectivity to light ends ($C_5$-$C_7$) was 36.9%.

Example 9

The same conditions were used as in Example 8, except a much lower I/O was targeted (7.6), more 2-chlorobutane promoter was used (0.03 g), and the reaction time was 60 minutes. Tributylmethylphosphonium heptachloroaluminate (TBMP-$Al_2Cl_7$) was used as the ionic liquid. The conversion was lower (52.2%) than in example 4, likely due to using low I/O, as were the $C_8$ selectivity (25.4%), RONC (83.2), and the TMP/DMH ratio (9.9). The selectivity to heavies ($C_{9+}$) was higher (66.5%), and selectivity to light ends ($C_5$-$C_7$) was lower (8.19%).

Example 10

The same conditions were used as in Example 9, but the reaction was completed at 0° C. The conversion was lower (35.8%) than in example 5, likely due to using lower temperature, but the $C_8$ selectivity (32.3%), RONC (84.7) were slightly higher, and the TMP/DMH ratio (20.2) was much higher, likely due to the lower temperature. The selectivity to heavies ($C_{9+}$) was slightly lower (60.0%), and selectivity to light ends ($C_5$-$C_7$) was lower (7.7%).

TABLE 3

Conditions and results for alkylation reactions of isobutane with 2-butenes using micro-emulsions

| | Example # | | | | | | |
|---|---|---|---|---|---|---|---|
| | Comp. 1 | Ex 1 | Ex 2 | Ex 3 | Ex 4 | Ex 5 | Ex 6 |
| Conditions | | | | | | | |
| IL | TBHP-Al2Cl7 | TBHP-Al2Cl7 | TBHP-Al2Cl7 | TBHP-Al2Cl7 | TBMP-Al2Cl7 | TBMP-Al2Cl7 | TBMP-Al2Cl7 |
| Temperature ° C. | 25 | 25 | 25 | 25 | 25 | 25 | 0 |
| IL g | 0.5 | 0.5 | 0.5 | 0.5 | 0.5 | 0.5 | 0.5 |
| CH2Cl2 g | — | 77 | 77 | 77 | 77 | 77 | 77 |
| n-hexane g | 39 | — | — | — | — | — | — |

TABLE 3-continued

Conditions and results for alkylation reactions of isobutane with 2-butenes using micro-emulsions

| | Example # | | | | | | |
|---|---|---|---|---|---|---|---|
| | Comp. 1 | Ex 1 | Ex 2 | Ex 3 | Ex 4 | Ex 5 | Ex 6 |
| iC4 g | 60 | 61 | 60 | 62 | 62 | 61 | 62 |
| Butenes fed (g) | 0.94 | 0.94 | 1.63 | 5.51 | 0.94 | 8 | 8 |
| target i/o (g/g) | 63.8 | 64.9 | 36.8 | 11.3 | 66 | 7.6 | 7.8 |
| target cat/o (g/g) | 0.54 | 0.53 | 0.3 | 0.09 | 0.53 | 0.06 | 0.06 |
| Olefin feed rate mL/hr | 6.88 | 6.88 | 10.32 | 3.33 | 6.88 | 14.37 | 14.37 |
| 2-chlorobutane g | 0.01 | 0.01 | 0 | 0.01 | 0.01 | 0.03 | 0.03 |
| Time min | 15 | 15 | 15 | 182 | 15 | 60 | 60 |
| Results | | | | | | | |
| Butenes Conversion % | 17.78 | 44.65 | 34.39 | 79.01 | 91.22 | 52.17 | 35.78 |
| mol butene converted/mol IL | 3.51 | 8.81 | 11.77 | 91.41 | 15.86 | 77.21 | 52.96 |
| mol butene converted/mol IL/hr | 14.04 | 35.25 | 47.08 | 30.14 | 63.45 | 77.21 | 52.96 |
| RONC | 80.11 | 85.81 | 87.23 | 90.35 | 93.99 | 83.22 | 84.65 |
| TMP/DMH | 5.02 | 13.17 | 10.51 | 14.87 | 26.5 | 9.94 | 20.23 |
| % Sel. C8s | 16.37 | 25.07 | 21.58 | 51.67 | 60.37 | 25.35 | 32.3 |
| % Sel. C9+s | 2.96 | 9.27 | 10.32 | 25.08 | 2.7 | 66.46 | 60.02 |
| % Sel. C5-C7s | 80.66 | 65.66 | 68.1 | 23.24 | 36.93 | 8.19 | 7.68 |

As used herein, the term about means within 10% of the value, or within 5%, or within 1%.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

Specific Embodiments

While the following is described in conjunction with specific embodiments, it will be understood that this description is intended to illustrate and not limit the scope of the preceding description and the appended claims.

A first embodiment of the invention is a process utilizing a micro-emulsion comprising forming the micro-emulsion comprising contacting an ionic liquid, a co-solvent, a hydrocarbon, an optional surfactant, and an optional catalyst promoter to form the micro-emulsion, the micro-emulsion comprising a hydrocarbon component comprising the hydrocarbon and an ionic liquid component comprising the ionic liquid, the ionic liquid comprising a halometallate anion and a cation, the co-solvent having a polarity greater than a polarity of the hydrocarbon, the ionic liquid being present in an amount of 0.05 wt % to 40 wt % of the micro-emulsion; and producing a product mixture in a process zone containing the micro-emulsion, the product mixture comprising a product. An embodiment of the invention is one, any or all of prior embodiments in this paragraph up through the first embodiment in this paragraph wherein the hydrocarbon comprises an isoparaffin having from 4 to 10 carbon atoms; and wherein producing the product mixture in the process zone comprises passing an olefin having from 2 to 8 carbon atoms to the process zone containing the micro-emulsion, the process zone being operated at alkylation reaction conditions to react the olefin and the isoparaffin to generate the product mixture and wherein the product comprises an alkylate. An embodiment of the invention is one, any or all of prior embodiments in this paragraph up through the first embodiment in this paragraph further comprising altering a composition of the product mixture to destroy the micro-emulsion; and separating the product from one or more of the ionic liquid, the co-solvent, and the isoparaffin. An embodiment of the invention is one, any or all of prior embodiments in this paragraph up through the first embodiment in this paragraph wherein the composition of the product mixture is altered by removing a portion of the co-solvent, increasing an amount of the hydrocarbon, increasing an amount of the product, adding an additional liquid having a polarity less than the polarity of the co-solvent, adding additional ionic liquid, or combinations thereof. An embodiment of the invention is one, any or all of prior embodiments in this paragraph up through the first embodiment in this paragraph wherein the micro-emulsion comprises micelles or reverse micelles and wherein more than about 90% of the micelles or reverse micelles have a diameter less than about 100 nanometers. An embodiment of the invention is one, any or all of prior embodiments in this paragraph up through the first embodiment in this paragraph wherein the product mixture is produced by one or more of alkylation, isomerization, di sproportionation, reverse di sproportionation, oligomerization, polymerization, cracking, and separation. An embodiment of the invention is one, any or all of prior embodiments in this paragraph up through the first embodiment in this paragraph wherein the cation of the ionic liquid comprises a tetraalkyl phosphonium cation, a dialkylimidazolium cation, an alkylimidazolium cation, a pyridinium cation, an alkyl pyridinium cation, a dialkylpyridinium cation, an alkylpyrrolidinium cation, a dialkylpyrrolidinium cation, a trialkylammonium cation, a tetraalkylammonium cation, a lactamium cation, an alkyl-lactamium cation, a trialkylsulfonium cation, or combinations thereof; and wherein the halometallate anion contains a metal selected from Al, Sc, Ti, V, Cr, Mn, Fe, Co, Ni, Cu, Zn, Ga, Y, Zr, Nb, Mo, In, Sn, Sb, La, Ce, Hf, Ta, W, or combinations thereof, and a halide selected from F, Cl, Br, I, or combinations thereof. An embodiment of the invention is one, any or all of prior embodiments in this paragraph up through the first embodiment in this paragraph wherein the co-solvent comprises a halogenated hydrocarbon, a halocarbon, a halogenated aromatic, an ether, an alcohol, an amide, an ester, a ketone, a nitrile, a sulfoxide, a sulfone, or combinations thereof. An embodiment of the invention is one, any or all of prior embodiments in this paragraph up through the first embodiment in this paragraph wherein the surfactant is present, wherein the surfactant comprises a quaternary ammonium salt, a ternary ammonium salt, a phosphonium salt, a sulfonate salt, a phosphonate salt, a disubstituted amide, an ether, or a glyme, and wherein a molar ratio of the surfactant to the ionic liquid is less than 2.51; or wherein the catalyst promoter is present, wherein the catalyst promoter comprises an anhydrous hydrogen halide, a halogenated hydrocarbon, or combinations thereof, and wherein a molar ratio of the catalyst promoter to the ionic liquid is 0.11 to 11; or both. An embodiment of the invention is one, any or all of prior embodiments in this paragraph up through the first embodiment in this paragraph wherein the ionic liquid is present in an amount of 0.05 wt % to 25 wt % of the micro-emulsion; the co-solvent is present in an amount of 30 wt % to 80 wt % of the micro-emulsion; or both. An embodiment of the invention is one, any or all of prior embodiments in this paragraph up through the first embodiment in this paragraph wherein a viscosity of the co-solvent is less than 1 centipoise at 25° C.

A second embodiment of the invention is a process comprising passing a micro-emulsion to an alkylation reactor, the micro-emulsion formed by contacting an ionic liquid, a co-solvent, an isoparaffin, an optional surfactant, and an optional catalyst promoter to form the micro-emulsion, the micro-emulsion comprising a hydrocarbon component comprising the isoparaffin, the isoparaffin having from 4 to 10 carbon atoms; an ionic liquid component comprising the ionic liquid, the ionic liquid comprising a halometallate anion and a cation; a co-solvent having a polarity greater than a polarity of the isoparaffin, the ionic liquid being present in an amount of about 0.05 wt % to about 40 wt % of the micro-emulsion; and passing an olefin having from 2 to 8 carbon atoms to the alkylation reactor containing the micro-emulsion, wherein the alkylation reactor is operated at alkylation reaction conditions to react the olefin and the isoparaffin to generate a reaction mixture comprising an alkylate. An embodiment of the invention is one, any or all of prior embodiments in this paragraph up through the second embodiment in this paragraph wherein one of more of the co-solvent is present in an amount of about 30 wt % to about 80 wt % of the micro-emulsion; a viscosity of the co-solvent is less than 1 centipoise at 25° C.; the ionic liquid is present in an amount of about 0.05 wt % to about 25 wt % of the micro-emulsion; or an overall molar ratio of isoparaffin to olefin is about 11 to about 1001. An embodiment of the invention is one, any or all of prior embodiments in this paragraph up through the second embodiment in this paragraph further comprising altering a composition of the reaction mixture by removing a portion of the co-solvent, increasing an amount of the isoparaffin, increasing an amount of alkylate, adding an additional liquid having a polarity less than the polarity of the co-solvent, adding ionic liquid, or combinations thereof to destroy the micro-emulsion; and separating the alkylate from one or more of the ionic liquid, the co-solvent, and the isoparaffin. An embodiment of the invention is one, any or all of prior embodiments in this paragraph up through the second embodiment in this paragraph wherein the cation of the ionic liquid comprises a tetraalkyl phosphonium cation, a dialkylimidazolium cation, an alkylimidazolium cation, a pyridinium cation, an alkyl pyridinium cation, a dialkylpyridinium cation, an alkylpyrrolidinium cation, a dialkylpyrrolidinium cation, a trialkylammonium cation, a tetraalkylammonium cation, a lactamium cation, an alkyllactamium cation, a trialkylsulfonium cation, or combinations thereof; and wherein the halometallate anion contains a metal selected from Al, Sc, Ti, V, Cr, Mn, Fe, Co, Ni, Cu, Zn, Ga, Y, Zr, Nb, Mo, In, Sn, Sb, La, Ce, Hf, Ta, W, or combinations thereof, and a halide selected from F, Cl, Br, I, or combinations thereof. An embodiment of the invention is one, any or all of prior embodiments in this paragraph up through the second embodiment in this paragraph, wherein additional mixing is applied and wherein a shear rate applied to the micro-emulsion is greater than about 300 inverse seconds, and a rate of olefin reaction is greater than about 20 mole olefin/mole ionic liquid/hour. An embodiment of the invention is one, any or all of prior embodiments in this paragraph up through the second embodiment in this paragraph, wherein the co-solvent comprises a halogenated hydrocarbon, a halocarbon, a halogenated aromatic, an ether, an alcohol, an amide, an ester, a ketone, a nitrile, a sulfoxide, a sulfone, or combinations thereof. An embodiment of the invention is one, any or all of prior embodiments in this paragraph up through the second embodiment in this paragraph, wherein surfactant is present, wherein the surfactant comprises a quaternary ammonium salt, a ternary ammonium salt, a phosphonium salt, a sulfonate salt, a phosphonate salt, a disubstituted amide, an ether, or a glyme, and wherein a molar ratio of the surfactant to the ionic liquid is less than about 2.51; or wherein the catalyst promoter is present, wherein the catalyst promoter comprises an anhydrous hydrogen halide, a halogenated hydrocarbon, or combinations thereof, and wherein a molar ratio of the catalyst promoter to the ionic liquid is about 0.11 to about 11; or both. An embodiment of the invention is one, any or all of prior embodiments in this paragraph up through the second embodiment in this paragraph, wherein the micro-emulsion comprises micelles or reverse micelles and wherein more than about 90% of the micelles or reverse micelles have a diameter less than about 100 nanometers. An embodiment of the invention is one, any or all of prior embodiments in this paragraph up through the second embodiment in this paragraph, wherein a selectivity to primary alkylation products is greater than about 50 wt %.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

What is claimed is:

1. A process utilizing a micro-emulsion comprising:
 forming the micro-emulsion comprising:
  contacting an ionic liquid, a co-solvent, a hydrocarbon, an optional surfactant, and an optional catalyst promoter to form the micro-emulsion, the micro-emulsion comprising a hydrocarbon component comprising the hydrocarbon and an ionic liquid component comprising the ionic liquid, the ionic liquid comprising a halometallate anion and a cation, the co-solvent having a polarity greater than a polarity of the hydrocarbon, the ionic liquid being present in an amount of 0.05 wt % to 40 wt % of the micro-emulsion; and producing a product mixture in a process zone containing the micro-emulsion, the product mixture comprising a product.

2. The process of claim 1 wherein the hydrocarbon comprises an isoparaffin having from 4 to 10 carbon atoms; and wherein producing the product mixture in the process zone comprises passing an olefin having from 2 to 8 carbon atoms to the process zone containing the micro-emulsion, the process zone being operated at alkylation reaction conditions to react the olefin and the isoparaffin to generate the product mixture and wherein the product comprises an alkylate.

3. The process of claim 1 further comprising:
altering a composition of the product mixture to destroy the micro-emulsion; and
separating the product from one or more of the ionic liquid, the co-solvent, and the hydrocarbon.

4. The process of claim 3 wherein the composition of the product mixture is altered by removing a portion of the co-solvent, increasing an amount of the hydrocarbon, increasing an amount of the product, adding an additional liquid having a polarity less than the polarity of the co-solvent, adding additional ionic liquid, or combinations thereof.

5. The process of claim 1 wherein the micro-emulsion comprises micelles or reverse micelles and wherein more than about 90% of the micelles or reverse micelles have a diameter less than about 100 nanometers.

6. The process of claim 1 wherein the product mixture is produced by one or more of alkylation, isomerization, disproportionation, reverse disproportionation, oligomerization, polymerization, cracking, and separation.

7. The process of claim 1 wherein the cation of the ionic liquid comprises a tetraalkyl phosphonium cation, a dialkylimidazolium cation, an alkylimidazolium cation, a pyridinium cation, an alkyl pyridinium cation, a dialkylpyridinium cation, an alkylpyrrolidinium cation, a dialkylpyrrolidinium cation, a trialkylammonium cation, a tetraalkylammonium cation, a lactamium cation, an alkyllactamium cation, a trialkylsulfonium cation, or combinations thereof; and wherein the halometallate anion contains a metal selected from Al, Sc, Ti, V, Cr, Mn, Fe, Co, Ni, Cu, Zn, Ga, Y, Zr, Nb, Mo, In, Sn, Sb, La, Ce, Hf, Ta, W, or combinations thereof, and a halide selected from F, Cl, Br, I, or combinations thereof.

8. The process of claim 1 wherein the co-solvent comprises a halogenated hydrocarbon, a halocarbon, a halogenated aromatic, an ether, an alcohol, an amide, an ester, a ketone, a nitrile, a sulfoxide, a sulfone, or combinations thereof.

9. The process of claim 1 wherein the surfactant is present, wherein the surfactant comprises a quaternary ammonium salt, a ternary ammonium salt, a phosphonium salt, a sulfonate salt, a phosphonate salt, a disubstituted amide, an ether, a glyme, and wherein a molar ratio of the surfactant to the ionic liquid is less than 2.5:1; or wherein the catalyst promoter is present, wherein the catalyst promoter comprises an anhydrous hydrogen halide, a halogenated hydrocarbon, or combinations thereof, and wherein a molar ratio of the catalyst promoter to the ionic liquid is 0.1:1 to 1:1; or both.

10. The process of claim 1 wherein the ionic liquid is present in an amount of 0.05 wt % to 25 wt % of the micro-emulsion; the co-solvent is present in an amount of 30 wt % to 80 wt % of the micro-emulsion; or both.

11. The process of claim 1 wherein a viscosity of the co-solvent is less than 1 centipoise at 25° C.

12. An alkylation process comprising:
passing a micro-emulsion to an alkylation reactor, the micro-emulsion formed by:
contacting an ionic liquid, a co-solvent, an isoparaffin, an optional surfactant, and an optional catalyst promoter to form the micro-emulsion, the micro-emulsion comprising: a hydrocarbon component comprising the isoparaffin, the isoparaffin having from 4 to 10 carbon atoms; an ionic liquid component comprising the ionic liquid, the ionic liquid comprising a halometallate anion and a cation; a co-solvent having a polarity greater than a polarity of the isoparaffin, the ionic liquid being present in an amount of about 0.05 wt % to about 40 wt % of the micro-emulsion; and
passing an olefin having from 2 to 8 carbon atoms to the alkylation reactor containing the micro-emulsion, wherein the alkylation reactor is operated at alkylation reaction conditions to react the olefin and the isoparaffin to generate a reaction mixture comprising an alkylate.

13. The process of claim 12 wherein one of more of: the co-solvent is present in an amount of about 30 wt % to about 80 wt % of the micro-emulsion; a viscosity of the co-solvent is less than 1 centipoise at 25° C.; the ionic liquid is present in an amount of about 0.05 wt % to about 25 wt % of the micro-emulsion; or an overall molar ratio of isoparaffin to olefin is about 1:1 to about 100:1.

14. The process of claim 12 further comprising:
altering a composition of the reaction mixture by removing a portion of the co-solvent, increasing an amount of the isoparaffin, increasing an amount of alkylate, adding an additional liquid having a polarity less than the polarity of the co-solvent, adding ionic liquid, or combinations thereof to destroy the micro-emulsion; and
separating the alkylate from one or more of the ionic liquid, the co-solvent, and the isoparaffin.

15. The process of claim 12 wherein the cation of the ionic liquid comprises a tetraalkyl phosphonium cation, a dialkylimidazolium cation, an alkylimidazolium cation, a pyridinium cation, an alkyl pyridinium cation, a dialkylpyridinium cation, an alkylpyrrolidinium cation, a dialkylpyrrolidinium cation, a trialkylammonium cation, a tetraalkylammonium cation, a lactamium cation, an alkyllactamium cation, a trialkylsulfonium cation, or combinations thereof; and wherein the halometallate anion contains a metal selected from Al, Sc, Ti, V, Cr, Mn, Fe, Co, Ni, Cu, Zn, Ga, Y, Zr, Nb, Mo, In, Sn, Sb, La, Ce, Hf, Ta, W, or combinations thereof, and a halide selected from F, Cl, Br, I, or combinations thereof.

16. The process of claim 12 wherein additional mixing is applied and wherein a shear rate applied to the micro-emulsion is greater than about 300 inverse seconds, and a rate of olefin reaction is greater than about 20 mole olefin/mole ionic liquid/hour.

17. The process of claim 12 wherein the co-solvent comprises a halogenated hydrocarbon, a halocarbon, a halogenated aromatic, an ether, an alcohol, an amide, an ester, a ketone, a nitrile, a sulfoxide, a sulfone, or combinations thereof.

18. The process of claim 12 wherein surfactant is present, wherein the surfactant comprises a quaternary ammonium salt, a ternary ammonium salt, a phosphonium salt, a sulfonate salt, a phosphonate salt, a disubstituted amide, an ether, or a glyme, and wherein a molar ratio of the surfactant to the ionic liquid is less than about 2.5:1; or wherein the catalyst promoter is present, wherein the catalyst promoter comprises an anhydrous hydrogen halide, a halogenated hydrocarbon, or combinations thereof, and wherein a molar ratio of the catalyst promoter to the ionic liquid is about 0.1:1 to about 1:1; or both.

19. The process of claim 12 wherein the micro-emulsion comprises micelles or reverse micelles and wherein more than about 90% of the micelles or reverse micelles have a diameter less than about 100 nanometers.

20. The process of claim 12 wherein a selectivity to primary alkylation products is greater than about 50 wt %.

* * * * *